US006440715B1

(12) United States Patent
Xu

(10) Patent No.: US 6,440,715 B1
(45) Date of Patent: Aug. 27, 2002

(54) **METHOD FOR CLONING AND EXPRESSION OF *RHODOTHERMUS OBAMENSIS* DNA POLYMERASE I LARGE FRAGMENT IN *E. COLI***

(75) Inventor: Shuang-yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/267,311

(22) Filed: Mar. 12, 1999

(51) Int. Cl.$^7$ ................................................. C12N 9/12
(52) U.S. Cl. .................... 435/194; 435/183; 435/252.3; 435/320.1; 530/350; 530/358
(58) Field of Search ............................. 435/194, 252.3, 435/183, 320.1; 530/350, 358

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis et al. | 435/91 |
| 4,800,159 A | 1/1989 | Mullis et al. | 435/172.3 |
| 4,889,818 A | 12/1989 | Gelfand et al. | 435/194 |
| 5,643,758 A | 7/1997 | Guan et al. | 435/69.7 |
| 5,834,247 A | 11/1998 | Comb et al. | 435/69.7 |
| 6,159,708 A | * 12/2000 | Sogo et al. | 435/69.1 |

FOREIGN PATENT DOCUMENTS

EP 0258017 8/1987

OTHER PUBLICATIONS

Blondal et al. EMBL/GenbankDDBJ databasse submissions Q9ZIG3, May, 1999.*
Stryer, Biochemistry, Freeman and Co. pubs., New York, NY, pp. 667–668, 1988.*
Joyce, C.M. et al, Methods in Enzymology, 262:3–13, (1995).
Nossal, N.G. et al, Methods in Enzymology, 262:560–569 (1995).
Aliotta, J.M. et al., Genetic Analysis: Biomol. Engin., 12:185–195 (1996).
Uemori, T. et al., J. Biochem., 113:401–410 (1993).
Milla, M.A et al., BioTechniques, 24:392–395 (1998).
Lawyer, F.C. et al., J. Biol. Chem., 264:6427–6437 (1989).
Asakura, K. et al., J. Ferment. Bioeng., 76:265–269 (1993).
Tabor, S. et al., Proc. Natl. Acad. Sci. USA, 92:6339–6343 (1995).
Vander Horn, P.B. et al., BioTechniques, 22:758–765 (1996).
Chien, A. et al., J. Bacteriol., 127:1550–1557 (1976).
Sako, Y. et al., Int. J. Syst. Bactriol., 46:1099–1104 (1996).
Blondal, T. et al., International Conference: Thermophile 98, Abstract,page G–P20.
Jung, S.E. et al., GenBank Accession No. AF030320 (1997).
Blondal et al., GenBank Accession No. AF028719 (1999).

* cited by examiner

*Primary Examiner*—Rebecca E. Prouty
*Assistant Examiner*—Richard Hutson
(74) *Attorney, Agent, or Firm*—Gregory D. Williams

(57) ABSTRACT

The present invention provides a novel thermostable DNA polymerase I obtainable from *Rhodothermus obamensis*, which possesses 3'-5' exonuclease activity and has a half-life of about 35 minutes at 94° C. This polymerase also contains a tyrosine residue in the ribosome binding site which improves incorporation of dideoxyribonucleic acids. Also provided are isolated DNA and vectors encoding this polymerase, as well as its large fragment, and methods for producing recombinant enzyme using the same.

6 Claims, 8 Drawing Sheets

FIG. 1A

```
     ATGCAGCGCCTGTACCTGATCGATGCCATGGCGCTGGCCTATCGGGCGCAATACGTGTTC
  1  ----------+----------+----------+----------+----------+----------+
      M  Q  R  L  Y  L  I  D  A  M  A  L  A  Y  R  A  Q  Y  V  F
     ATCAGCCGGCCGCTTGTCAACTCGAAGGGACAGAACACCTCGGCCGCCTACGGTTTTACG
 61  ----------+----------+----------+----------+----------+----------+
      I  S  R  P  L  V  N  S  K  G  Q  N  T  S  A  A  Y  G  F  T
     ACCTCCCTTCTGAAGCTGATCGAAGAACACGGCATGGACTACATGGCCGTGGTCTTCGAC
121  ----------+----------+----------+----------+----------+----------+
      T  S  L  L  K  L  I  E  E  H  G  M  D  Y  M  A  V  V  F  D
     GCCGGCGGGGAGGAGGGCACGTTTCGCGAAGCGATCTATGAGGAATACAAGGCGCATCGG
181  ----------+----------+----------+----------+----------+----------+
      A  G  G  E  E  G  T  F  R  E  A  I  Y  E  E  Y  K  A  H  R
     GAGCCGCCGCCGGAAGATCTGCTGGCCAACCTGCCCTGGATCAAGGAGATCGTCCGGGCG
241  ----------+----------+----------+----------+----------+----------+
      E  P  P  P  E  D  L  L  A  N  L  P  W  I  K  E  I  V  R  A
     CTGGACATTCCCGTCATCGAGGAGCCGGGCGTCGAGGCCGACGACGTGATCGGAACGCTG
301  ----------+----------+----------+----------+----------+----------+
      L  D  I  P  V  I  E  E  P  G  V  E  A  D  D  V  I  G  T  L
     GCCCGTCGGGCCGAGGCGCACGGCATCGACGTGGTGATCGTCTCACCCGACAAGGACTTT
361  ----------+----------+----------+----------+----------+----------+
      A  R  R  A  E  A  H  G  I  D  V  V  I  V  S  P  D  K  D  F
     CTGCAGCTGCTGAGCCCGCACGTTTCCATCTACAAACCGGCGCGGCGCGGCGAAACCTTC
421  ----------+----------+----------+----------+----------+----------+
      L  Q  L  L  S  P  H  V  S  I  Y  K  P  A  R  R  G  E  T  F
     GACCTGATCACCATCGAGACTTTCCGGGAGACCTACGGCCTGGAGCCGCACCAGTTCATC
481  ----------+----------+----------+----------+----------+----------+
      D  L  I  T  I  E  T  F  R  E  T  Y  G  L  E  P  H  Q  F  I
     GACGTGCTGGCTCTCATGGGCGATCCGAGCGACAATGTGCCGGGCGTGCCGGGCATCGGC
541  ----------+----------+----------+----------+----------+----------+
      D  V  L  A  L  M  G  D  P  S  D  N  V  P  G  V  P  G  I  G
     GAAAAGACCGCCGTGCAGCTCATCCAACAGTACGGCTCGGTGGAAAACCTGCTGGCCCAT
601  ----------+----------+----------+----------+----------+----------+
      E  K  T  A  V  Q  L  I  Q  Q  Y  G  S  V  E  N  L  L  A  H
     GCCGAGGAGGTGAAAGGGAAGCGGGCCCGCGAGGGGCTCCTGAACCACCGCGAGGAAGCG
661  ----------+----------+----------+----------+----------+----------+
      A  E  E  V  K  G  K  R  A  R  E  G  L  L  N  H  R  E  E  A
     CTCCTCTCGAAGCGGCTGGTGACGATCCGGACCGATGTGCCGTTGCGCATTCGCTGGGAG
721  ----------+----------+----------+----------+----------+----------+
      L  L  S  K  R  L  V  T  I  R  T  D  V  P  L  R  I  R  W  E
     GCGTTCCATCGCGCCCGGCCCGATCTGCCGCGCCTGCTGCAGATCTTTCAGGAGCTGGAA
781  ----------+----------+----------+----------+----------+----------+
      A  F  H  R  A  R  P  D  L  P  R  L  L  Q  I  F  Q  E  L  E
     TTCGACTCGCTGGTGCGGCGCATCCGGGAAGGCGGACTGGCCGGCATTGTGAACGGCGAA
841  ----------+----------+----------+----------+----------+----------+
      F  D  S  L  V  R  R  I  R  E  G  G  L  A  G  I  V  N  G  E
     GCCGCCTTGGATGAGGCGCTTGAAGCGGAGACCGAGCCGGAGTTCGATTTCGGGCCaTAC
901  ----------+----------+----------+----------+----------+----------+
      A  A  L  D  E  A  L  E  A  E  T  E  P  E  F  D  F  G  P  Y
     GAGCCGCTGCAGGTGTACGATCCGGAAAAGGCGGACTACCGGATCGTCCGCAACCGCCAG
961  ----------+----------+----------+----------+----------+----------+
      E  P  L  Q  V  Y  D  P  E  K  A  D  Y  R  I  V  R  N  R  Q
```

FIG. 1B

```
     CAGCTCGACGAACTCGTGGCGCATCTGGACGGATTCGAACGGCTGGCCATCGACACGGAG
1021 ---------+---------+---------+---------+---------+---------+
     Q  L  D  E  L  V  A  H  L  D  G  F  E  R  L  A  I  D  T  E

ACGACTTCGACCGAGGCCATGTGGGCCTCGCTGGTGGGCATTGCCTTTTCCTGGGAGAAA
1081 ---------+---------+---------+---------+---------+---------+
     T  T  S  T  E  A  M  W  A  S  L  V  G  I  A  F  S  W  E  K

GGCCAGGGCTACTACGTGCCCACGCCGCTGCCGGACGGCACGCCGACCGAGACGGTGCTC
1141 ---------+---------+---------+---------+---------+---------+
     G  Q  G  Y  Y  V  P  T  P  L  P  D  G  T  P  T  E  T  V  L

GAGCGACTGGCGCCGATCCTCCGACGGGCGCAGCGCAAAGTCGGTCAGAACCTGAAGTAC
1201 ---------+---------+---------+---------+---------+---------+
     E  R  L  A  P  I  L  R  R  A  Q  R  K  V  G  Q  N  L  K  Y

GATCTGGTGGTGCTGGCGCGGCACGGCGTCCAAGTCCCGCCCCCGTACTTCGACACGATG
1261 ---------+---------+---------+---------+---------+---------+
     D  L  V  V  L  A  R  H  G  V  Q  V  P  P  P  Y  F  D  T  M

GTGGCGCACTACCTGATTGCGCCCGAGGAACCGCATAACCTGGACGTGCTGGCCCGCCAG
1321 ---------+---------+---------+---------+---------+---------+
     V  A  H  Y  L  I  A  P  E  E  P  H  N  L  D  V  L  A  R  Q

TACCTTCGCTACCAGATGGTTTCCATCACGGAACTGATCGGCTCGGGTCGCGACCAGAAG
1381 ---------+---------+---------+---------+---------+---------+
     Y  L  R  Y  Q  M  V  S  I  T  E  L  I  G  S  G  R  D  Q  K

TCCATGCGCGACGTGTCGATCGACGAGGTGGGGCCCTATGCCTGTGAAGACACGGACATT
1441 ---------+---------+---------+---------+---------+---------+
     S  M  R  D  V  S  I  D  E  V  G  P  Y  A  C  E  D  T  D  I

GCGCTGCAACTGGCCGATGTGCTGGCCGCCGAGTTGGACCGACACGGACTCCGGCATATC
1501 ---------+---------+---------+---------+---------+---------+
     A  L  Q  L  A  D  V  L  A  A  E  L  D  R  H  G  L  R  H  I

GCCGAGGAGATGGAGTTCCCGCTCATCGAGGTGCTGGCCGATATGGAGCGGACGGGCATC
1561 ---------+---------+---------+---------+---------+---------+
     A  E  E  M  E  F  P  L  I  E  V  L  A  D  M  E  R  T  G  I

TGCATCGATCGCGCGGTGCTTCGGGAAATCGGTAAGCAACTCGAAGCGGAGCTTCACGAA
1621 ---------+---------+---------+---------+---------+---------+
     C  I  D  R  A  V  L  R  E  I  G  K  Q  L  E  A  E  L  H  E

CTGGAGGTGAAGATCTATGAGGTGGCCGGCGTCGAATTCAACATCGGCTCGCCGCAGCAA
1681 ---------+---------+---------+---------+---------+---------+
     L  E  V  K  I  Y  E  V  A  G  V  E  F  N  I  G  S  P  Q  Q

CTGGCGGACGTCTTGTTCAAGAAGCTCGGGTTGAAGCCGCGGGCGCGCACCAGCACCGGC
1741 ---------+---------+---------+---------+---------+---------+
     L  A  D  V  L  F  K  K  L  G  L  K  P  R  A  R  T  S  T  G

CGGCCTTCCACCAAAGAGAGCGTGCTGCAGGAGCTGGCCACGCAGCACCCGCTCCCCGGC
1801 ---------+---------+---------+---------+---------+---------+
     R  P  S  T  K  E  S  V  L  Q  E  L  A  T  Q  H  P  L  P  G

CTGATCCTGGACTGGCGACACCTGGCCAAGCTCAAAAGCACCTACGTGGACGGCCTCGAG
1861 ---------+---------+---------+---------+---------+---------+
     L  I  L  D  W  R  H  L  A  K  L  K  S  T  Y  V  D  G  L  E

CCGCTCATCCATCCGGAGACCGGCCGCATCCACACCACGTTCAACCAGACGGTGACGGCT
1921 ---------+---------+---------+---------+---------+---------+
     P  L  I  H  P  E  T  G  R  I  H  T  T  F  N  Q  T  V  T  A

ACCGGGCGGCTTTCCTCGAGCAACCCGAACCTGCAGAACATCCCGGTTCGCACCGAGATG
1981 ---------+---------+---------+---------+---------+---------+
     T  G  R  L  S  S  S  N  P  N  L  Q  N  I  P  V  R  T  E  M
```

FIG. 1C

```
     GGGCGGGAGATCCGCAGGGCGTTTGTGCCGCGGCCGGGCTGGAAGCTGCTCTCGGCCGAC
2041 ---------+---------+---------+---------+---------+---------+
     G  R  E  I  R  R  A  F  V  P  R  P  G  W  K  L  L  S  A  D
     TACGTCCAGATCGAACTTCGCATTCTGGCCGCGCTGAGCGGCGACGAGGCGCTTCGCCGG
2101 ---------+---------+---------+---------+---------+---------+
     Y  V  Q  I  E  L  R  I  L  A  A  L  S  G  D  E  A  L  R  R
     GCCTTTCTGGAGGGACAGGACATCCATACGGCCACGGcAGCCCGCGTCTTCAAGGTGCCG
2161 ---------+---------+---------+---------+---------+---------+
     A  F  L  E  G  Q  D  I  H  T  A  T  A  A  R  V  F  K  V  P
     CCCGAGCAGGTgAcgCCCGAGCAGCGCCGCCGCGCCAAGATGGTCAACTACGGCATTCCC
2221 ---------+---------+---------+---------+---------+---------+
     P  E  Q  V  T  P  E  Q  R  R  R  A  K  M  V  N  Y  G  I  P
     TACGGGATTTCGGCCTGGGGGCTGGCGCAGCGGCTTCGCTGCTCCACGCGCGAGGCGCAG
2281 ---------+---------+---------+---------+---------+---------+
     Y  G  I  S  A  W  G  L  A  Q  R  L  R  C  S  T  R  E  A  Q
     GAGCTTATCGAAGAATATCAGCGGGCCTTTCCGGGCGTGACGCGCTACCTGCACCGCGTC
2341 ---------+---------+---------+---------+---------+---------+
     E  L  I  E  E  Y  Q  R  A  F  P  G  V  T  R  Y  L  H  R  V
     GTCGAAGAGGCCCGCCAGAAGGGCTACGTCGAGACGCTGCTGGGCCGCCGCCGCTACGTA
2401 ---------+---------+---------+---------+---------+---------+
     V  E  E  A  R  Q  K  G  Y  V  E  T  L  L  G  R  R  R  Y  V
     CCGAACATCAACTCCCGCAACCGGGCCGAGCGCTCGATGGCCGAACGCATCGCCGTGAAC
2461 ---------+---------+---------+---------+---------+---------+
     P  N  I  N  S  R  N  R  A  E  R  S  M  A  E  R  I  A  V  N
     ATGCCCATCCAGGGCACGCAGGCCGACATGATCAAGCTGGCCATGGTGCACATCTACCAC
2521 ---------+---------+---------+---------+---------+---------+
     M  P  I  Q  G  T  Q  A  D  M  I  K  L  A  M  V  H  I  Y  H
     CGACTGAAGCGGGAAGGCTACCGGGCCAAGATGCTGCTCCAGGTGCACGACGAGCTGGTC
2581 ---------+---------+---------+---------+---------+---------+
     R  L  K  R  E  G  Y  R  A  K  M  L  L  Q  V  H  D  E  L  V
     TTCGAGATGCCCCCCGAAGAGGTGGAGCCCGTGCGCCAACTGGTCGAGCAGGAGATGAAG
2641 ---------+---------+---------+---------+---------+---------+
     F  E  M  P  P  E  E  V  E  P  V  R  Q  L  V  E  Q  E  M  K
     CAGGCCCTGCCGCTGGAAGGTGTGCCCATCGAGGTGGACATCGGCGTCGGCGACAACTGG
2701 ---------+---------+---------+---------+---------+---------+
     Q  A  L  P  L  E  G  V  P  I  E  V  D  I  G  V  G  D  N  W
     CTGGATGCCCACTGA
2761 ---------+----- 2775
     L  D  A  H
```

FIG. 2A

```
    ATGAACGGCGAAGCCGCCTTGGATGAGGCGCTTGAAGCGGAGACCGAGCCGGAGTTCGAT
  1 ---------+---------+---------+---------+---------+---------+
    M  N  G  E  A  A  L  D  E  A  L  E  A  E  T  E  P  E  F  D
    TTCGGGCCaTACGAGCCGCTGCAGGTGTACGATCCGGAAAAGGCGGACTACCGGATCGTC
 61 ---------+---------+---------+---------+---------+---------+
    F  G  P  Y  E  P  L  Q  V  Y  D  P  E  K  A  D  Y  R  I  V
    CGCAACCGCCAGCAGCTCCACGAACTCGTGGCGCATCTGGACGGATTCGAACGGCTGGCC
121 ---------+---------+---------+---------+---------+---------+
    R  N  R  Q  Q  L  D  E  L  V  A  H  L  D  G  F  E  R  L  A
    ATCGACACGGAGACGACTTCGACCGAGGCCATGTGGGCCTCGCTGGTGGGCATTGCCTTT
181 ---------+---------+---------+---------+---------+---------+
    I  D  T  E  T  T  S  T  E  A  M  W  A  S  L  V  G  I  A  F
    TCCTGGGAGAAAGGCCAGGGCTACTACGTGCCCACGCCGCTGCCGGACGGCACGCCGACC
241 ---------+---------+---------+---------+---------+---------+
    S  W  E  K  G  Q  G  Y  Y  V  P  T  P  L  P  D  G  T  P  T
    GAGACGGTGCTCGAGCGACTGGCGCCGATCCTCCGACGGGCGCAGCGCAAAGTCGGTCAG
301 ---------+---------+---------+---------+---------+---------+
    E  T  V  L  E  R  L  A  P  I  L  R  R  A  Q  R  K  V  G  Q
    AACCTGAAGTACGATCTGGTGGTGCTGGCGCGGCACGGCGTCCAAGTCCCGCCCCCGTAC
361 ---------+---------+---------+---------+---------+---------+
    N  L  K  Y  D  L  V  V  L  A  R  H  G  V  Q  V  P  P  P  Y
    TTCGACACGATGGTGGCGCACTACCTGATTGCGCCCGAGGAACCGCATAACCTGGACGTG
421 ---------+---------+---------+---------+---------+---------+
    F  D  T  M  V  A  H  Y  L  I  A  P  E  E  P  H  N  L  D  V
    CTGGCCCGCCAGTACCTTCGCTACCAGATGGTTTCCATCACGGAACTGATCGGCTCGGGT
481 ---------+---------+---------+---------+---------+---------+
    L  A  R  Q  Y  L  R  Y  Q  M  V  S  I  T  E  L  I  G  S  G
    CGCGACCAGAAGTCCATGCGCGACGTGTCGATCGACGAGGTGGGGCCCTATGCCTGTGAA
541 ---------+---------+---------+---------+---------+---------+
    R  D  Q  K  S  M  R  D  V  S  I  D  E  V  G  P  Y  A  C  E
    GACACGGACATTGCGCTGCAACTGGCCGATGTGCTGGCCGCCGAGTTGGACCGACACGGA
601 ---------+---------+---------+---------+---------+---------+
    D  T  D  I  A  L  Q  L  A  D  V  L  A  A  E  L  D  R  H  G
    CTCCGGCATATCGCCGAGGAGATGGAGTTCCCGCTCATCGAGGTGCTGGCCGATATGGAG
661 ---------+---------+---------+---------+---------+---------+
    L  R  H  I  A  E  E  M  E  F  P  L  I  E  V  L  A  D  M  E
    CGGACGGGCATCTGCATCGATCGCGCGGTGCTTCGGGAAATCGGTAAGCAACTCGAAGCG
721 ---------+---------+---------+---------+---------+---------+
    R  T  G  I  C  I  D  R  A  V  L  R  E  I  G  K  Q  L  E  A
    GAGCTTCACGAACTGGAGGTGAAGATCTATGAGGTGGCCGGCGTCGAATTCAACATCGGC
781 ---------+---------+---------+---------+---------+---------+
    E  L  H  E  L  E  V  K  I  Y  E  V  A  G  V  E  F  N  I  G
    TCGCCGCAGCAACTGGCGGACGTCTTGTTCAAGAAGCTCGGGTTGAAGCCGCGGGCGCGC
841 ---------+---------+---------+---------+---------+---------+
    S  P  Q  Q  L  A  D  V  L  F  K  K  L  G  L  K  P  R  A  R
    ACCAGCACCGGCCGGCCTTCCACCAAAGAGAGCGTGCTGCAGGAGCTGGCCACGCAGCAC
901 ---------+---------+---------+---------+---------+---------+
    T  S  T  G  R  P  S  T  K  E  S  V  L  Q  E  L  A  T  Q  H
    CCGCTCCCCGGCCTGATCCTGGACTGGCGACACCTGGCCAAGCTCAAAAGCACCTACGTG
961 ---------+---------+---------+---------+---------+---------+
    P  L  P  G  L  I  L  D  W  R  H  L  A  K  L  K  S  T  Y  V
```

FIG. 2B

```
     GACGGCCTCGAGCCGCTCATCCATCCGGAGACCGGCCGCATCCACACCACGTTCAACCAG
1021 ------------------------------------------------------------+
     D  G  L  E  P  L  I  H  P  E  T  G  R  I  H  T  T  F  N  Q
     ACGGTGACGGCTACCGGGCGGCTTTCCTCGAGCAACCCGAACCTGCAGAACATCCCGGTT
1081 ------------------------------------------------------------+
     T  V  T  A  T  G  R  L  S  S  S  N  P  N  L  Q  N  I  P  V
     CGCACCGAGATGGGGCGGGAGATCCGCAGGGCGTTTGTGCCGCGGCCGGGCTGGAAGCTG
1141 ------------------------------------------------------------+
     R  T  E  M  G  R  E  I  R  R  A  F  V  P  R  P  G  W  K  L
     CTCTCGGCCGACTACGTCCAGATCGAACTTCGCATTCTGGCCGCGCTGAGCGGCGACGAG
1201 ------------------------------------------------------------+
     L  S  A  D  Y  V  Q  I  E  L  R  I  L  A  A  L  S  G  D  E
     GCGCTTCGCCGGGCCTTTCTGGAGGGACAGGACATCCATACGGCCACGGcAGCCCGCGTC
1261 ------------------------------------------------------------+
     A  L  R  R  A  F  L  E  G  Q  D  I  H  T  A  T  A  A  R  V
     TTCAAGGTGCCGCCCGAGCAGGTgAcgCLCGAGCAGCGCCGCCGCGCCAAGATGGTCAAC
1321 ------------------------------------------------------------+
     F  K  V  P  P  E  Q  V  T  P  E  Q  R  R  R  A  K  M  V  N
     TACGGCATTCCCTACGGGATTTCGGCCTGGGGGCTGGCGCAGCGGCTTCGCTGCTCCACG
1381 ------------------------------------------------------------+
     Y  G  I  P  Y  G  I  S  A  W  G  L  A  Q  R  L  R  C  S  T
     CGCGAGGCGCAGGAGCTTATCGAAGAATATCAGCGGGCCTTTCCGGGCGTGACGCGCTAC
1441 ------------------------------------------------------------+
     R  E  A  Q  E  L  I  E  E  Y  Q  R  A  F  P  G  V  T  R  Y
     CTGCACCGCGTCGTCGAAGAGGCCCGCCAGAAGGGCTACGTCGAGACGCTGCTGGGCCGC
1501 ------------------------------------------------------------+
     L  H  R  V  V  E  E  A  R  Q  K  G  Y  V  E  T  L  L  G  R
     CGCCGCTACGTACCGAACATCAACTCCCGCAACCGGGCCGAGCGCTCGATGGCCGAACGC
1561 ------------------------------------------------------------+
     R  R  Y  V  P  N  I  N  S  R  N  R  A  E  R  S  M  A  E  R
     ATCGCCGTGAACATGCCCATCCAGGGCACGCAGGCCGACATGATCAAGCTGGCCATGGTG
1621 ------------------------------------------------------------+
     I  A  V  N  M  P  I  Q  G  T  Q  A  D  M  I  K  L  A  M  V
     CACATCTACCACCGACTGAAGCGGGAAGGCTACCGGGCCAAGATGCTGCTCCAGGTGCAC
1681 ------------------------------------------------------------+
     H  I  Y  H  R  L  K  R  E  G  Y  R  A  K  M  L  L  Q  V  H
     GACGAGCTGGTCTTCGAGATGCCCCCCGAAGAGGTGGAGCCCGTGCGCCAACTGGTCGAG
1741 ------------------------------------------------------------+
     D  E  L  V  F  E  M  P  P  E  E  V  E  P  V  R  Q  L  V  E
     CAGGAGATGAAGCAGGCCCTGCCGCTGGAAGGTGTGCCCATCGAGGTGGACATCGGCGTC
1801 ------------------------------------------------------------+
     Q  E  M  K  Q  A  L  P  L  E  G  V  P  I  E  V  D  I  G  V
     GGCGACAACTGGCTGGATGCCCACTGA
1861 ---------------------------  1887
     G  D  N  W  L  D  A  H  *
```

METHOD FOR CLONING AND EXPRESSION OF *RHODOTHERMUS OBAMENSIS* DNA POLYMERASE I LARGE FRAGMENT IN *E. COLI*

BACKGROUND OF INVENTION

The present invention relates to a novel thermostable DNA polymerase I from *Rhodothermus obamensis*, which possesses 3'-5' exonuclease activity and has a preliminary estimated half-life of 35 minutes at 94° C., as well as methods for cloning and producing the large fragment of *R. obamensis* DNA polymerase I, as well as isolated DNA encoding this enzyme and vectors containing the same.

DNA polymerases are important enzymes involved in chromosome replication and repair. These enzymes have also been employed in DNA diagnostics and analysis. In several of these applications, including PCR, thermocycle sequencing, and iso-thermal strand displacement amplification, DNA polymerases must maintain enzymatic activity at temperatures from 50° C.–95° C. One advantageous source for such polymerases is thermophiles. Here we describe a method for purifying, cloning and expressing *Rhodothermus obamensis* DNA polymerase I large fragment in *E. coli*.

*E. coli* DNA polymerase I and T4 DNA polymerase were cloned, purified and characterized previously (Joyce C. M. and Derbyshire V. *Methods in Enzymology*, 262:3–13, (1995); Nossal N. G. et al. *Methods in Enzymology*, 262: 560–569, (1995)). These enzymes have a variety of uses in recombinant DNA technology including DNA labeling by nick translation, second-strand cDNA synthesis in cDNA cloning, and DNA sequencing.

U.S. Pat. Nos. 4,683,195, 4,683,202 and 4,800,159 disclosed the use of DNA polymerases in a process for amplifying, detecting, and/or cloning nucleic acid sequences. This process, commonly referred to as polymerase chain reaction (PCR), involves the use of a polymerase, primers and nucleotide triphosphates and amplifying existing nucleic acid sequences.

A number of thermostable DNA polymerases have been isolated and cloned from thermophilic eubacteria. The thermostable Bst DNA polymerase from *Bacillus stearothermophilus* and the Bca DNA polymerase from *Bacillus caldotenax* have been cloned and expressed in *E. coli* (Aliotta J. M. et al. *Genetic Analysis: Biomol. Engin*, 12:185–195, (1996); Uemori, T. et al. *J. Biochem.* 113:401–410, (1993)). These two DNA polymerases have been used in strand displacement amplification (Milla, M. A. et al. *Biotechniques*, 24:392–395, (1998)).

DNA polymerases have also been cloned from a number of Thermus species such as *T. aquaticus* (Lawyer, F. C., et al. *J. Biol. Chem.* 264:6427–6437 (1989)). *T. thermophilus* (Asakura, K. et al. *J. Ferment. Bioeng.*, 76:265–269, (1993), and *T. filiformis* (Jung, S. E. et al. GenBank Accession No. AF030320, (1997)). These characterized Thermus DNA polymerases, belonging to the Family A DNA polymerases, exhibit 5'-3' exonuclease activity while lacking 3'-5' proofreading exonuclease activity. For thermocycling sequencing, a Taq DNA polymerase variant called ThermoSequenase (F667Y) has been constructed that efficiently incorporates dideoxy terminators and dye-terminators (Tabor S. and Richardson C. C.,*Proc. Natl. Acad. Sci. USA*, 92:6339–6343, (1995); Vander Horn P. B. et al. *Biotechniques*, 22:758–765, (1996)). Although readable DNA sequence for one sequencing reaction has improved from 300 bp to about 600 bp, further technical improvements are needed to achieve 1000 or more bases of reliable sequence for each reaction. Such improvement most likely requires the introduction of new DNA polymerases such as thermostable T7-like DNA polymerases.

Research was conducted on the isolation and purification of DNA polymerases from Thermus aquaticus (Chien, A. et al. *J. Bacteriol.* 127:1550–1557, (1976)). The publication of Chien, A. et al. discloses the isolation and purification of a DNA polymerase with a temperature optimum of 80° C. from *T. aquaticus* YT1 strain. The Chien et al., purification procedure involves a four-step process. These steps include preparation of crude extract, DEAE-Sephadex chromatography, phosphocellulose chromatography and chromatography on DNA cellulose.

U.S. Pat. No. 4,889,818 discloses a purified thermostable DNA polymerase from *T. aquaticus*, Taq DNA polymerase, having a molecular weight of about 86,000 to 90,000 daltons prepared by a process substantially identical to the process of Kaledin with the addition of the substitution of a phosphocellulose chromatography step in lieu of chromatography on single-strand DNA-cellulose. In addition, European Patent Application 0258017 disclose Taq polymerase as the preferred enzyme for use in the PCR process discussed above. Research has indicated that while the Taq DNA polymerase has a 5'-3' polymerase-dependent exonuclease function, Taq DNA polymerase does not possess a 3'-5' proofreading exonuclease function (Lawyer, F. C., et al. J. Biol. Chem. 264:6427–6437 (1989)). As a result, Taq DNA polymerase is prone to base incorporation errors, making its use in certain applications undesirable. For example, attempting to clone an amplified gene is problematic since any one copy of the gene may contain an error due to a random misincorporation event. Depending on where in the replication cycle that error occurs (e.g., in an early replication cycle), the entire DNA amplified could contain the erroneously incorporated base, thus, giving rise to a mutated gene product.

Accordingly, it would be desirable to clone and produce a thermostable DNA polymerase with 3'-5' proof-reading exonuclease activity that may be used to improve the fidelity of DNA amplification reactions described above. It would also be desirable to clone a thermostable and processive DNA polymerase which efficiently incorporates dye terminators.

SUMMARY OF THE INVENTION

In accordance with the present invention, there is provided a novel thermostable DNA polymerase I from *Rhodothermus obamensis*, which possesses 3'-5' exonuclease activity and has a preliminarily estimated half-life of 35 minutes at 94° C. This thermostable enzyme obtainable from *Rhodothermus obamensis*, a thermophile isolated from a shallow marine hydrothermal vent in Tachibana Bay, Japan, has a molecular weight of about 104 kDa, and possesses a tyrosine residue in the ribosome binding domain which increases the incorporation rate of dideoxynucleotides.

Also provided by the instant invention are methods for cloning and producing the large fragment of *R. obamensis* DNA polymerase I, as well as isolated DNA encoding this enzyme and vectors containing the same. The *Rhodothermus obamensis* DNA polymerase I large fragment has a molecular weight of about 71 kDa.

BRIEF DESCRIPTION OF THE DRAWINGS

FIG. 1 is the nucleotide sequence (SEQ ID NO:1) and the predicted amino acid sequences (SEQ ID NO:2) of *R. obamensis* DNA polymerase I.

FIG. 2 is the nucleotide sequence (SEQ ID NO:3) and the predicted amino acid sequences (SEQ ID NO:4) of *R. obamensis* DNA polymerase I large fragment.

DETAILED DESCRIPTION OF THE INVENTION

Figure 3:
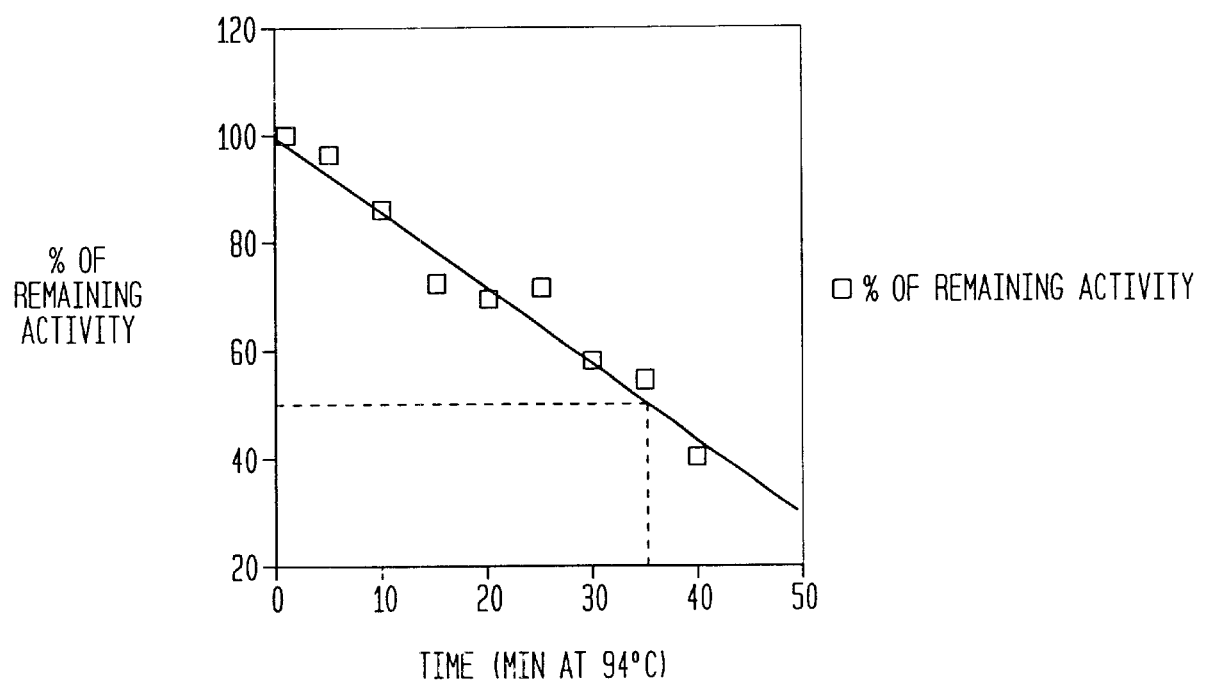
FIGS. 3A and B is the SDS-PAGE gel showing the purification steps for recombinant *R. obamensis* DNA polymerase I large fragment. Lane 1 and 3, IPTG-induced cell extract after heat treatment; lane 2 and 4, non-induced cell extract after heat treatment; lane 5 and 7, protein size marker (7 to 212 kDa); lane 6, partially purified recombinant *R. obamensis* DNA polymerase I large fragment. Arrow I, indicating recombinant *R. obamensis* DNA polymerase I large fragment; arrow II indicating *E. coli* GroEL protein.

*Rhodothermus obamensis* was isolated from a shallow marine hydrothermal vent in Tachibana Bay, Japan. It can grow in the temperature range of 50 to 85° C. with optimal growth temperature at 80° C. The pH range for growth media is pH 5.5 to 9.0. It can be cultured in a marine broth with NaCl concentration of 1 to 5%. In a preferred embodiment, the type strain is *Rhodothermus obamensis* OKD7 (Sako Y. et al. *Int. J. Syst. Bactriol.* 46:1099–1104, (1996)).

Purification of *R. Obamensis* DNA Polymerase I

The native or recombinant *R. obamensis* DNA polymerase can be purified by the following procedure:

Cells are resuspended in a lysis buffer (50 mM Tris-HCl, pH 8, 1 mM EDTA, 5 mM DTT) and lysed by sonication. Pulverized ammonium sulfate is added slowly with gentle stirring to a final concentration of 30% (w/v), and the suspension is allowed to sit at 4° C. overnight. The ammonium sulfate precipitate is collected by centrifugation in a rotor at 12,000 rpm for 30 min. The supernatant is discarded. The pellet is resuspended in a buffer containing 50 mM Tris-HCl, pH 8, 10% glycerol, 1 mM EDTA, 5 mM DTT. The *R. obamensis* DNA polymerase I may be further purified by chromatography, for example:

*R. obamensis* DNA polymerase I may be purified by phosphocellulose chromatography (Whatman cellulose phosphate ion-exchange resin P11). Fractions may be assayed for thermostable DNA polymerase activity and peak fractions may be pooled and dialysed.

*R. obamensis* DNA polymerase I may be purified by DEAE chromatography (Whatman ion exchange cellulose DE52 resin). Fractions may then be assayed for thermostable DNA polymerase activity and peak fractions can be pooled and dialysed.

*R. obamensis* DNA polymerase I may be purified, as in a preferred embodiment, by DNA binding affinity column chromatography (Heparin sepharose or Heparin TSK). Fractions may be assayed for thermostable DNA polymerase activity, and peak fractions may be pooled and dialysed.

*R. obamensis* DNA polymerase I can be purified by Mono Q FPLC. Fractions may be assayed for thermostable DNA polymerase activity. Peak fractions may be pooled and dialysed.

*R. obamensis* DNA polymerase I may be further purified by Mono S FPLC. Fractions may then be assayed for thermostable DNA polymerase activity, and peak fractions can be pooled and dialysed in a storage buffer with 50% glycerol.

Alternatively, recombinant *R. obamensis* DNA polymerase I may be purified by affinity purification via the use of a fusion protein. For example, fusion of *R. obamensis* DNA polymerase I to maltose binding protein, chitin binding protein, GST, or His tag. After the fusion protein is purified, the affinity tag may be removed by a protease or by controlled protein splicing/cleavage reaction. (U.S. Pat. Nos. 5,643,758 and 5,834,247.)

Cloning of *R. Obamensis* DNA Polymerase I

The method described herein by which the *R. obamensis* DNA polymerase I gene is cloned and its large fragment is expressed includes the following steps:

1. The genomic DNA is purified from *R. obamensis* cells.

2. Conserved regions in DNA polymerase I are found by nucleotide sequence comparison of Pol I type DNA polymerases from Eubacteria and especially thermophilic bacteria. Based on the conserved sequences, one set of degenerate primers is designed and an initial PCR is carried out using the degenerate primers to amplify part of the *R. obamensis* DNA polymerase I. A 609 bp DNA fragment in the DNA polymerase domain is amplified and sequenced.

3. Single stranded DNA primers are designed based on the initial 609 bp sequence. Inverse PCR is used to amplify upstream and downstream DNA sequences. *R. obamensis* genomic DNA is digested with restriction enzymes with 4–6 bp recognition sequences, giving rise to reasonable size template DNA for inverse PCR reactions. The digested DNA is self-ligated at a low DNA concentration. The ligated circular DNA is used as templates for inverse PCR reaction using a set of primers that annealed to the left or right ends of the initial fragment. The inverse PCR products are purified in low-melting agarose gel and sequenced directly using primers. The newly derived DNA sequences are compared with sequences in GenBank using BlastX program. This step is repeated until the start codon was found upstream and stop codon was found downstream. The entire DNA polymerase gene is found to be 2772 bp long, encoding a protein with predicted molecular weight of 104.7 kDa.

4. The 3'-5' exonuclease domain is compared with that of *E. coli* DNA polymerase I. It is found that *R. obamensis* DNA polymerase I contains three conserved motifs of 3'-5' exonuclease. The three conserved motifs have the following amino acid sequence: motif I, DTE, motif II, NLKYD, motif III, YACED. It is concluded that *R. obamensis* DNA polymerase I may contain 3'-5' exonuclease proofreading activity. In addition, *R. obamensis* DNA polymerase I contains a Tyr residue (Y761) in the ribose binding region (*E. coli* O helix homolog). It's known that Tyr residue at this position increases the incorporation rate for dideoxynucleotides.

5. To overexpress the large fragment of *R. obamensis* DNA polymerase I, 888-bp DNA encoding N-terminus 5'-3' exonuclease domain is deleted by PCR. The deletion variant lacking 5'-3' exonuclease region is 1884 bp long, encoding the 628-aa DNA polymerase I large fragment with predicted molecular weight of 71.3 kDa. This *R. obamensis* DNA polymerase I large fragment is similar to *E. coli* Klenow fragment, but it contains 28 extra amino acid residues at the N-terminus. The DNA coding for the large fragment is amplified by PCR, digested with NdeI and BamHI and cloned into a T7 expression vector pAII17. One clone #7 is further characterized.

6. *E. coli* cells ER2566 [pAII17-Rob polI large fragment] is cultured to late log phase and induced by addition of IPTG (*R. obamensis* is abbreviated as Rob). Cell extract is prepared and heated at 65° C. for 30 min. Heat-denatured *E. coli* proteins were removed by centrifugation and the supernatant is assayed at 65° C. for DNA polymerase activity on activated calf thymus DNA. It is found that the large fragment has thermostable DNA polymerase activity.

7. R. obamensis DNA polymerase I large fragment is purified by chromatography through Heparin-Sepharose column. The large fragment is partially purified. Another protein of 60 kDa is copurified with R. obamensis DNA polymerase I large fragment. To determine if this 60 kDa protein is a protease degradation product, the N-terminus of the 60 kDa protein is sequenced. The first 15 residues are compared with known proteins in protein data base. It has 100% identity to E. coli GroEL protein.

8. To determine the half-life of the partially purified large fragment, the protein is heated at 94° C. for 1 to 40 min. Samples are taken and assayed for remaining DNA polymerase activity. It is found that R. obamensis DNA polymerase I large fragment has an half-life of 35 min at 94° C.

The following Examples are given to illustrate embodiments of the present invention as it is presently preferred to practice. It will be understood that these Examples are illustrative, and that the invention is not to be considered as restricted thereto as indicated in the appended claims.

The references cited above and below are herein incorporated by reference.

EXAMPLE I

Cloning of R. obamensis DNA Polymerase I Gene

Rhodothermus obamensis (JCM 9785, Japan Collection of Microorganisms, Wako-shi, Saitama, Japan) was cultured in Bacto marine broth at 70° C. overnight. Cells from one liter of culture were collected by centrifugation. Genomic DNA was prepared from the cell pellet by the standard procedure. A set of degenerate primers were designed based on the conserved amino acid sequence in the DNA polymerase domain. The primers have the following sequences:

5'-TCCGA(C/T)CCCAACCT(G/C)CAGAACATCC(SEQ ID NO:5)

5'-AGGA(G/C)(G/C)AGCTCGTCGTG(G/C)ACCT(SEQ ID NO:6)

(G/C) indicates degenerate position, G or C.

Primers 138–151 and 138–152 were used to amplify a portion of R. obamensis DNA polymerase I in PCR under the following condition: 95° C. for 30 sec, 50° C. for 1 min, 72° C. for 1 min, 35 cycles, 2.5 units of Taq plus Vent® DNA polymerase (50:1 ratio). A ~600 bp PCR product was found. The PCR product was gel-purified in low-melting agarose gel and sequenced directly by thermocycling sequencing using primer 138–151 which generated a 609 bp DNA fragment. When this DNA fragment was translated into amino acid sequence and compared to known proteins in GenBank, it was found that it has 50% aa sequence identity to E. coli DNA polymerase I (pol I) and 54% aa sequence identity to Taq DNA polymerase.

Two primers were synthesized based on the known 609 bp DNA sequence. They have the following sequences:

5'-CGCAGGGCGTTTGTGCCGCGG-3' 202–154 (SEQ ID NO:7)

5'-GTCTCCCGCCCCATCTCGGTG-3' 202–155 (SEQ ID NO:8)

R. obamensis genomic DNA was digested individually with the following restriction enzymes: AvaI, BsaAI, BsaHI, BstNI, EagI, HaeII, HhaI, HincII, MspI, NcoI, NspI, SacII, Sau3AI, TaqI, TseI, Tsp45I, BanI, or AluI. After restriction digestion, the DNA was purified by phenol-CHCl₃ extraction and ethanol precipitation. The digested DNA was self-ligated at a low DNA concentration (2 ug/ml). T4 DNA ligase was inactivated by heating at 65° C. for 30 min and the DNA was precipitated and resuspended in TE buffer. The self-ligated genomic DNA was used in inverse PCR to amplify the remaining portion of the DNA polymerase I gene. The following condition was used in inverse PCR: 95° C. for 30 sec, 55° C. for 30 sec, and 72° C. for 2 min, 30 cycles. Inverse PCR products were found in BsaHI, HaeII, NcoI, and NspI digested and self-ligated DNA templates. The NcoI inverse PCR fragment was the largest, giving rise to about 1950 bp of new DNA sequence (2550 bp–600 bp=~1950 bp). This fragment was gel-purified in low-melting agarose gel and sequenced directly using primers 202–154 and 202–155. Four new primers were made to finish sequencing the NcoI fragment.

Two new inverse PCR primers were made to amplify the DNA beyond the NcoI site. The two primers have the following sequences:

5'-GCCGGCCGCTTGTCAACTCGA-3' 205–7 (SEQ ID NO:9)

5'-TGATGAACACGTATTGCGCCC-3' 205–8 (SEQ ID NO:10)

R. obamensis genomic DNA was digested with restriction enzymes AvaI, BsaHI, BstNI, SacII, Sau3AI, TaqI, TseI, Tsp45I, BanI, AluI and self-ligated as described above. The ligated genomic DNA was used in inverse PCR. Inverse PCR condition was 95° C. for 30 sec, 55° C. for 30 sec, and 72° C. for 2 min, 35 cycles. Inverse PCR products were found in Sau3AI, TaqI, and TseI digested and self-ligated DNA. The inverse PCR products were gel-purified and sequenced which gave rise to 27 bp of new DNA sequence. A start codon was found in the newly derived sequence.

To amplify the C-terminus coding region of R. obamensis DNA polymerase I, two inverse PCR primers were made:

5'-GAAGCGGGAAGGCTACCGGGCCAA-3' 204 (SEQ ID NO:11)

5'-AGTCGGTGGTAGATGTGCACCATG-3' 204 (SEQ ID NO:12)

Inverse PCR condition was 95° C. for 30 sec, 55° C. for 30 sec. and 72° C. for 2 min, 35 cycles. Inverse PCR products were found in HaeII, NspI, Sau3AI, and Tsp45I digested and self-ligated templates. The inverse PCR products were gel-purified and sequenced which gave rise to the C-terminus coding region. The entire R. obamensis DNA polymerase gene is 2772 bp long, encoding a protein with predicted molecular weight of 104.7 kDa (FIG. 1). Unlike Taq DNA polymerase, R. obamensis DNA polymerase I contains three conserved 3'-5' exonuclease motifs. The three conserved motifs have the following amino acid sequence:

motif I, DTE
motif II, NLKYD
motif III, YACED.

It is concluded that R. obamensis DNA polymerase I may contain 3'-5' exonuclease proofreading activity. In addition, R. obamensis DNA polymerase I contains a Tyr residue (Y761) in the ribose binding region (E. coli O helix homolog). It's known that Tyr residue at this position increases the incorporation rate for dideoxynucleotides. Pol I-like DNA polymerases that have a Tyr residue at the ribose selectivity site include DNA polymerases from phage T7 and T3, yeast mitochondria, Mycobacterium tuberculosis, Mycobacterium leprae, Rhodothermus obamensis, and Rhodothermus sp. 'ITI518'.

EXAMPLE II

Expression of R. obamensis DNA Polymerase I Large Fragment

To construct a large fragment of R. obamensis DNA polymerase I, 888-bp DNA encoding N-terminus 51–3' exonuclease domain was deleted. The deletion variant lacking 5'-3' exonuclease region is 1884 bp long, encoding 628-aa DNA polymerase I large fragment with predicted molecular weight of 71.3 kDa. This R. obamensis DNA polymerase I large fragment is similar to E. coli Klenow fragment, but it contains 28 extra amino acid residues at the N-terminus (FIG. 2). The DNA coding for the large fragment was amplified by PCR under the PCR condition of 95° C. for 30 sec, 55° C. for 30 sec. and 72° C. for 2 min, 20 cycles, 2 units of Vent® DNA polymerase. The PCR primers have the following sequence:

5'-CTGGCCGGCCATATGAACGGCGAAGCCGCCTTG GAT-
GAG-3' 204–146. (CATATG=NdeI site). (SEQ ID NO:13)

5'-GTTGGATCCGCTTCAGTGGGCATCCAGCCAGTTGTC-3'
204–147. (GGATCC=BamHI site). (SEQ ID NO:14)

The amplified PCR product was digested with NdeI and BamHI and inserted into a T7 expression vector pAII17 precut with NdeI and BamHI. The ligated DNA was used to transform E. coli competent cell ER2566. Eighteen $Amp^R$ transformants were screened for insert. Six plasmids contained the correct size insert (#2, #5, #6, #7, #12, and #14). To test DNA polymerase activity in all six isolates, E. coli cells ER2566 [pAII17-Rob-polI-large fragment] were cultured to late log phase and induced by addition of IPTG to 0.5 mM concentration (R. obamensis is abbreviated as Rob). Cell extract was prepared by sonication and centrifugation. The cleared lysate was heated at 65° C. for 30 min. Heat-denatured E. coli proteins were removed by centrifugation and the supernatant was analyzed on an SDS-PAGE gel (FIG. 3, lanes 1–4) and was assayed at 65° C. for DNA polymerase activity on activated calf thymus DNA. The DNA polymerase activity was performed in a total of 50 ul volume at 65° C. It contains 20 ul of cell extract, 5 ul (10 ug) of activated calf thymus DNA, 1 ul of dNTP (5.4 mM), 5 ul of 10× thermopol buffer, 1 ul of [$^3$H]TTP, 18 ul of $sdH_2O$. The components of 1× Thermopol buffer are 10 mM KCl, 20 mM Tris-HCl, pH 8.8, 10 mM $(NH_4)_2SO_4$, 2 mM $MgSO_4$, 0.1% Triton X-100. Following incubation at 65° C. for 20–30 min, the entire volume was spotted on to DE81 membrane discs and dried under a heating lamp for 30 min. The membranes were washed 2× in 500 ml of 10% TCA. The acid-insoluble [$^3$H]TMP incorporated DNA was counted in scintillation counting solution. It was found that isolates #2, #5, #7, #12, and #14 have thermostable DNA polymerase activity. #7 and #12 displayed highest activity. #7 was chosen to be further characterized. Two liters of cells of #7 clone were induced with IPTG and cell extract was prepared by sonication and centrifugation. The cell extract was heated at 65° C. for 30 min and the denatured E. coli proteins were removed by centrifugation. R. obamensis DNA polymerase I large fragment was purified by chromatography through Heparin-Sepharose column. R. obamensis DNA polymerase I large fragment was eluted with 50 mM to 1 M NaCl gradient. Fractions 19 and 20 contained the most DNA polymerase activity. Proteins from fractions 15 to 20 were analyzed on an SDS-PAG gel. Two major proteins were found, one with expected size of 71 kDa. Another protein of 60 kDa is copurified with R. obamensis DNA polymerase I large fragment (FIG. 3, lane 6). To determine if this 60 kDa protein was a protease degradation product, the N-terminus of the 60 kDa protein was sequenced. The first 15 residues (AAKDVKFGNDARVKM (SEQ ID NO:15)) are compared with protein data base. It has 100% identity to E. coli GroEL protein. It was concluded that the 60 kDa protein is not a protease degradation product. Since R. obamensis DNA polymerase I large fragment is a foreign protein to E. coli, perhaps it needs more GroEL protein to help it to fold correctly.

To increase stability of the T7 expression clone, ER2566 [pLysS] was transformed with the plasmid carrying Rob polI large fragment. The final expression strain is ER2566 [pAII17-Rob polI large fragment, pLysS], $Amp^R$ and $Cm^R$.

A sample of the E. coli containing ER2566[pAII17-Rob polI large fragment, pLysS], (NEB#1186) has been deposited under the terms and conditions of the Budapest Treaty with the American Type Culture Collection on Mar. 12, 1999 and received ATCC Accession No. 207168.

To determine the half-life of the partially purified large fragment, the protein is heated at 94° C. for 1 to 40 min. Samples are taken and assayed for remaining DNA polymerase activity. DNA polymerase assay was about the same as described above except that 5 ul of the heat-treated large fragment was used in the assay. The time of heat treatment was plotted against the percentage of remaining DNA polymerase activity. It was found that R. obamensis DNA polymerase I large fragment has an half-life of 35 min at 94° C. (FIG. 4).

During the course of this work, the DNA polymerase I gene was cloned from Rhodothermus sp. 'ITI5181' and was released in GenBank on Jan. 1, 1999 (Blondal et al., GenBank Accession No. AF028719). Rhodothermus obamensis and Rhodothermus sp. 'ITI518' DNA polymerase I share 98% amino acid sequence identity. However, the thermostability of Rhodothermus obamensis and Rhodothermus sp. 'ITI518' DNA polymerase I large fragments are different. It was reported that the half-life of Rhodothermus sp. 'ITI518' DNA polymerase I large fragment at 90° C. is about 10 min (Blondal, T. et al. International Conference: Thermophile 98, Abstract, page G-P20). R. obamensis DNA polymerase I large fragment is more thermostable. It has an half-life of 35 min at 94° C. There are two possible explanations. One possibility is that R. obamensis DNA polymerase I large fragment has a different N-terminus than Rhodothermus sp. 'ITI518' DNA polymerase I large fragment (due to different aa deletion in the 5'-3' exonuclease region). It's known that N-terminus deletion of 5'-3' exonuclease domain can increase thermostability of DNA polymerases. The second possibility is that R. obamensis DNA polymerase I large fragment fortuitously copurified with E. coli protein GroEL, which is a chaperon for protein folding. The inclusion of GroEL protein in the polymerase assay may increase the thermostability of R. obamensis DNA polymerase I large fragment at 94° C.

EXAMPLE III

Expression of R. obamensis DNA Polymerase I and Its Large Fragment in Any Expression Host R. obamensis DNA polymerase I gene or its deletion derivative can be amplified by PCR using primers. The deletion can be in the 5'-3' or 3'-5' exonuclease domains. Alternatively, the active site residues of 5'-3' or 3'-5' exonuclease domains can mutagenized without affecting the DNA polymerase domain. Restriction sites can be engineered in the PCR primers to aid the cloning of the PCR products into appropriate cloning vectors. PCR conditions can be 90–95° C. for 30 sec, 50–65° C. for 30 sec. and 72° C. for 1–3 min, 20–30 cycles, 1–5 units of Vent® DNA polymerase or any proofreading DNA polymerase. PCR products can be digested with appropriate restriction enzymes. After ligation of PCR products to vectors, the ligated DNA can be used to transform expression host by transformation or electroporation. Plasmid mini-preparations can be made to screen inserts. Once the correct inserts are found, cells can be induced to produce the desired proteins. Cell extract can be prepared by lysozyme treatment or sonication and centrifugation. The cleared lysate can be heated at 65–85° C. for 30–60 min. Heat-denatured *E. coli* proteins can be removed by centrifugation and the supernatant can be analyzed on an SDS-PAG gel. The lysate can be assayed at 65–85° C. for DNA polymerase activity on activated calf thymus DNA or single-stranded DNA with a primer. The DNA polymerase activity can be performed in a total of 50–100 ul volume at 65–85° C. It contains 1–20 ul of cell extract, 5 ul (10 ug) of activated calf thymus DNA, 1 ul of dNTP (5.4 mM), 5 ul of 10× thermopol buffer or any DNA polymerase buffer, 1 ul of [$^3$H]TTP, 18 ul of sdH$_2$O. The components of 1× Thermopol buffer are 10 mM KCl, 20 mM Tris-HCl, pH 8.8, 10 mM (NH$_4$)$_2$SO$_4$, 2 mM MgSO$_4$, 0.1% Triton X-100. Following incubation at 65–85° C. for 10–30 min, the entire volume can be spotted on to DE81 membrane discs and dried. The membranes can be washed 1–2× in 500 ml of 10% TCA. The acid-insoluble [$^3$H]TMP incorporated DNA can be counted in scintillation counting solution. *R. obamensis* DNA polymerase I and its large fragments can be purified by chromatography through affinity column, cation/anion exchange columns, or gel filtration columns.

To determine the half-life of the partially purified large fragment, the protein can be heated at 94° C. for 1 to 60 min. Samples can be taken and assayed for remaining DNA polymerase activity. The time course can be plotted against the percentage of remaining DNA polymerase activity. Heat shock proteins such as GroEL chaperon can be added to the polymerase reaction to increase the thermostability of DNA polymerase.

What is claimed is:

1. A substantially pure thermostable DNA polymerase I obtainable from *Rhodothermus obamensis* (JCM 9785), wherein said polymerase possesses 3'-5' exonuclease activity and has a half-life of about 35 minutes at 94° C.

2. The substantially pure thermostable DNA polymerase I of claim 1, wherein said polymerase has a molecular weight of about 104 kDa.

3. The substantially pure DNA polymerase I of claim 1, wherein said polymerase is encoded by a DNA segment comprising the DNA sequence of SEQ ID NO: 1 or mutants or variants of said DNA sequence.

4. A recombinant *R. obamensis* DNA polymerase I, wherein said polymerase I has a molecular weight of about 104 kDa, possesses 3'-5' exonuclease activity and has a half-life of about 35 minutes at 94° C.

5. A recombinant *R. obamensis* DNA polymerase I large fragment, wherein said polymerase I large fragment has a molecular weight of about 71 kDa, possesses 3'-5' exonuclease activity and has a half-life of about 35 minutes at 94° C.

6. A DNA polymerase I composition comprising the recombinant *R. obamensis* DNA polymerase I large fragment of claim 5 and an approximately 60 kDa *E. coli* GroEL protein, wherein the thermostability of said polymerase I large fragment is increased by the presence of said GroEL protein.

* * * * *

UNITED STATES PATENT AND TRADEMARK OFFICE
CERTIFICATE OF CORRECTION

PATENT NO. : 6,440,715 B1
DATED : August 27, 2002
INVENTOR(S) : Xu

Figure 4A:
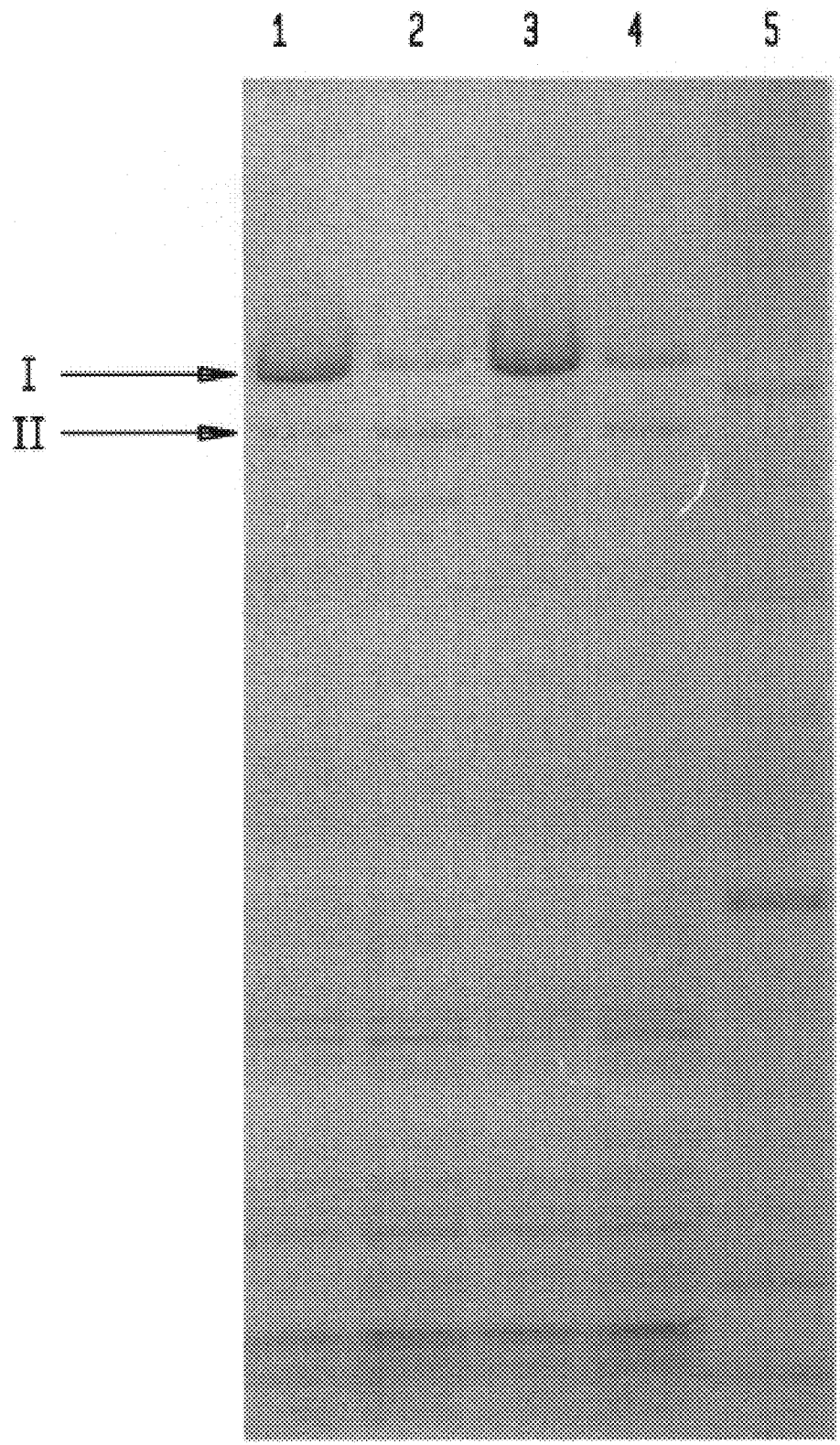
FIG. 4 illustrates the thermostability of the recombinant *R. obamensis* DNA polymerase I large fragment at 94° C. The polymerase assay was carried out at 65° C. for 20 min after incubation of the DNA polymerase at 94° C. for 1 to 40 min.
Figure 4B:
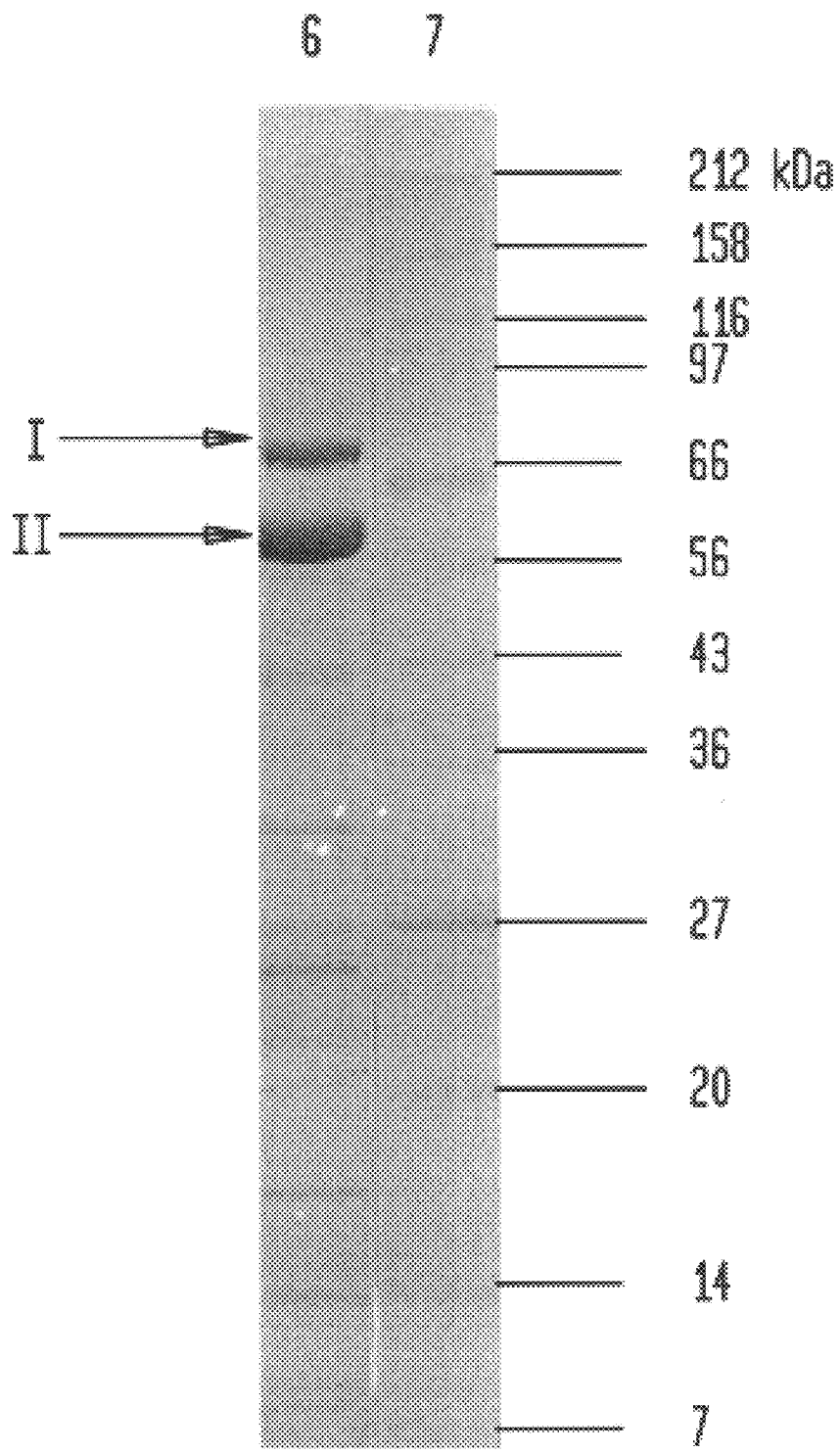

It is certified that error appears in the above-identified patent and that said Letters Patent is hereby corrected as shown below:

Column 3,
Line 4, replace "FIGS. 3A and B" with -- FIGS. 4A and B --.
Line 13, replace "FIG. 4" with -- FIG. 3 --.

Column 5,
Line 36, replace "C(SEQ ID NO15)" with -- C-3' 138-151 (SEQ ID NO:5) --
Line 38, replace "CT(SEQIDNO6)" with -- CTG-3' 138-152 (SEQ ID NO:6) --

Column 6,
Line 32, replace "3' 204SEQ ID NO:11)" with -- 3' 204-7 (SEQ ID NO:11) --
Line 34, replace "204-SEQ ID NO:12)" with -- 204-8 (SEQ ID NO:12) --
Line 67, replace "51-3'" with -- 5'-3' --

Column 7,
Line 31, replace "(FIG. 3, lanes 1-4)" with -- (FIG. 4A, lanes 1-4) --.
Line 60, replace "(FIG. 3, lane 6)" with -- (FIG. 4B, lane 6) --.

Column 8,
Line 21, replace "(FIG. 4)" with -- (FIG. 3) --.

Signed and Sealed this

Twenty-fourth Day of December, 2002

JAMES E. ROGAN
*Director of the United States Patent and Trademark Office*

SEQUENCE LISTING

```
<160> NUMBER OF SEQ ID NOS: 15

<210> SEQ ID NO 1
<211> LENGTH: 2775
<212> TYPE: DNA
<213> ORGANISM: Rhodothermus obamensis
<220> FEATURE:
<221> NAME/KEY: CDS
<222> LOCATION: (1)..(2772)

<400> SEQUENCE: 1 atg cag cgc ctg tac ctg atc gat gcc atg gcg ctg gcc tat cgg gcg      48
Met Gln Arg Leu Tyr Leu Ile Asp Ala Met Ala Leu Ala Tyr Arg Ala
 1               5                  10                  15 caa tac gtg ttc atc agc cgg ccg ctt gtc aac tcg aag gga cag aac      96
Gln Tyr Val Phe Ile Ser Arg Pro Leu Val Asn Ser Lys Gly Gln Asn
            20                  25                  30 acc tcg gcc gcc tac ggt ttt acg acc tcc ctt ctg aag ctg atc gaa     144
Thr Ser Ala Ala Tyr Gly Phe Thr Thr Ser Leu Leu Lys Leu Ile Glu
        35                  40                  45 gaa cac ggc atg gac tac atg gcc gtg gtc ttc gac gcc ggc ggg gag     192
Glu His Gly Met Asp Tyr Met Ala Val Val Phe Asp Ala Gly Gly Glu
    50                  55                  60 gag ggc acg ttt cgc gaa gcg atc tat gag gaa tac aag gcg cat cgg     240
Glu Gly Thr Phe Arg Glu Ala Ile Tyr Glu Glu Tyr Lys Ala His Arg
 65                 70                  75                  80 gag ccg ccg ccg gaa gat ctg ctg gcc aac ctg ccc tgg atc aag gag     288
Glu Pro Pro Pro Glu Asp Leu Leu Ala Asn Leu Pro Trp Ile Lys Glu
                85                  90                  95 atc gtc cgg gcg ctg gac att ccc gtc atc gag gag ccg ggc gtc gag     336
Ile Val Arg Ala Leu Asp Ile Pro Val Ile Glu Glu Pro Gly Val Glu
            100                 105                 110 gcc gac gac gtg atc gga acg ctg gcc cgt cgg gcc gag gcg cac ggc     384
Ala Asp Asp Val Ile Gly Thr Leu Ala Arg Arg Ala Glu Ala His Gly
        115                 120                 125 atc gac gtg gtg atc gtc tca ccc gac aag gac ttt ctg cag ctg ctg     432
Ile Asp Val Val Ile Val Ser Pro Asp Lys Asp Phe Leu Gln Leu Leu
    130                 135                 140 agc ccg cac gtt tcc atc tac aaa ccg gcg cgg cgc ggc gaa acc ttc     480
Ser Pro His Val Ser Ile Tyr Lys Pro Ala Arg Arg Gly Glu Thr Phe
145                 150                 155                 160 gac ctg atc acc atc gag act ttc cgg gag acc tac ggc ctg gag ccg     528
Asp Leu Ile Thr Ile Glu Thr Phe Arg Glu Thr Tyr Gly Leu Glu Pro
                165                 170                 175
```

-continued

```
cac cag ttc atc gac gtg ctg gct ctc atg ggc gat ccg agc gac aat      576
His Gln Phe Ile Asp Val Leu Ala Leu Met Gly Asp Pro Ser Asp Asn
            180                 185                 190 gtg ccg ggc gtg ccg ggc atc ggc gaa aag acc gcc gtg cag ctc atc      624
Val Pro Gly Val Pro Gly Ile Gly Glu Lys Thr Ala Val Gln Leu Ile
                195                 200                 205 caa cag tac ggc tcg gtg gaa aac ctg ctg gcc cat gcc gag gag gtg      672
Gln Gln Tyr Gly Ser Val Glu Asn Leu Leu Ala His Ala Glu Glu Val
        210                 215                 220 aaa ggg aag cgg gcc cgc gag ggg ctc ctg aac cac cgc gag gaa gcg      720
Lys Gly Lys Arg Ala Arg Glu Gly Leu Leu Asn His Arg Glu Glu Ala
225                 230                 235                 240 ctc ctc tcg aag cgg ctg gtg acg atc cgg acc gat gtg ccg ttg cgc      768
Leu Leu Ser Lys Arg Leu Val Thr Ile Arg Thr Asp Val Pro Leu Arg
                245                 250                 255 att cgc tgg gag gcg ttc cat cgc gcc cgg ccc gat ctg ccg cgc ctg      816
Ile Arg Trp Glu Ala Phe His Arg Ala Arg Pro Asp Leu Pro Arg Leu
            260                 265                 270 ctg cag atc ttt cag gag ctg gaa ttc gac tcg ctg gtg cgg cgc atc      864
Leu Gln Ile Phe Gln Glu Leu Glu Phe Asp Ser Leu Val Arg Arg Ile
        275                 280                 285 cgg gaa ggc gga ctg gcc ggc att gtg aac ggc gaa gcc gcc ttg gat      912
Arg Glu Gly Gly Leu Ala Gly Ile Val Asn Gly Glu Ala Ala Leu Asp
290                 295                 300 gag gcg ctt gaa gcg gag acc gag ccg gag ttc gat ttc ggg cca tac      960
Glu Ala Leu Glu Ala Glu Thr Glu Pro Glu Phe Asp Phe Gly Pro Tyr
305                 310                 315                 320 gag ccg ctg cag gtg tac gat ccg gaa aag gcg gac tac cgg atc gtc     1008
Glu Pro Leu Gln Val Tyr Asp Pro Glu Lys Ala Asp Tyr Arg Ile Val
                325                 330                 335 cgc aac cgc cag cag ctc gac gaa ctc gtg gcg cat ctg gac gga ttc     1056
Arg Asn Arg Gln Gln Leu Asp Glu Leu Val Ala His Leu Asp Gly Phe
            340                 345                 350 gaa cgg ctg gcc atc gac acg gag acg act tcg acc gag gcc atg tgg     1104
Glu Arg Leu Ala Ile Asp Thr Glu Thr Thr Ser Thr Glu Ala Met Trp
        355                 360                 365 gcc tcg ctg gtg ggc att gcc ttt tcc tgg gag aaa ggc cag ggc tac     1152
Ala Ser Leu Val Gly Ile Ala Phe Ser Trp Glu Lys Gly Gln Gly Tyr
370                 375                 380 tac gtg ccc acg ccg ctg ccg gac ggc acg ccg acc gag acg gtg ctc     1200
Tyr Val Pro Thr Pro Leu Pro Asp Gly Thr Pro Thr Glu Thr Val Leu
385                 390                 395                 400 gag cga ctg gcg ccg atc ctc cga cgg gcg cag cgc aaa gtc ggt cag     1248
Glu Arg Leu Ala Pro Ile Leu Arg Arg Ala Gln Arg Lys Val Gly Gln
                405                 410                 415 aac ctg aag tac gat ctg gtg gtg ctg gcg cgg cac ggc gtc caa gtc     1296
Asn Leu Lys Tyr Asp Leu Val Val Leu Ala Arg His Gly Val Gln Val
            420                 425                 430 ccg ccc ccg tac ttc gac acg atg gtg gcg cac tac ctg att gcg ccc     1344
Pro Pro Pro Tyr Phe Asp Thr Met Val Ala His Tyr Leu Ile Ala Pro
        435                 440                 445 gag gaa ccg cat aac ctg gac gtg ctg gcc cgc cag tac ctt cgc tac     1392
Glu Glu Pro His Asn Leu Asp Val Leu Ala Arg Gln Tyr Leu Arg Tyr
450                 455                 460 cag atg gtt tcc atc acg gaa ctg atc ggc tcg ggt cgc gac cag aag     1440
Gln Met Val Ser Ile Thr Glu Leu Ile Gly Ser Gly Arg Asp Gln Lys
465                 470                 475                 480 tcc atg cgc gac gtg tcg atc gac gag gtg ggg ccc tat gcc tgt gaa     1488
Ser Met Arg Asp Val Ser Ile Asp Glu Val Gly Pro Tyr Ala Cys Glu
```

-continued

```
                 485                 490                 495
gac acg gac att gcg ctg caa ctg gcc gat gtg ctg gcc gcc gag ttg        1536
Asp Thr Asp Ile Ala Leu Gln Leu Ala Asp Val Leu Ala Ala Glu Leu
            500                 505                 510 gac cga cac gga ctc cgg cat atc gcc gag gag atg gag ttc ccg ctc        1584
Asp Arg His Gly Leu Arg His Ile Ala Glu Glu Met Glu Phe Pro Leu
        515                 520                 525 atc gag gtg ctg gcc gat atg gag cgg acg ggc atc tgc atc gat cgc        1632
Ile Glu Val Leu Ala Asp Met Glu Arg Thr Gly Ile Cys Ile Asp Arg
    530                 535                 540 gcg gtg ctt cgg gaa atc ggt aag caa ctc gaa gcg gag ctt cac gaa        1680
Ala Val Leu Arg Glu Ile Gly Lys Gln Leu Glu Ala Glu Leu His Glu
545                 550                 555                 560 ctg gag gtg aag atc tat gag gtg gcc ggc gtc gaa ttc aac atc ggc        1728
Leu Glu Val Lys Ile Tyr Glu Val Ala Gly Val Glu Phe Asn Ile Gly
                565                 570                 575 tcg ccg cag caa ctg gcg gac gtc ttg ttc aag aag ctc ggg ttg aag        1776
Ser Pro Gln Gln Leu Ala Asp Val Leu Phe Lys Lys Leu Gly Leu Lys
            580                 585                 590 ccg cgg gcg cgc acc agc acc ggc cgg cct tcc acc aaa gag agc gtg        1824
Pro Arg Ala Arg Thr Ser Thr Gly Arg Pro Ser Thr Lys Glu Ser Val
        595                 600                 605 ctg cag gag ctg gcc acg cag cac ccg ctc ccc ggc ctg atc ctg gac        1872
Leu Gln Glu Leu Ala Thr Gln His Pro Leu Pro Gly Leu Ile Leu Asp
    610                 615                 620 tgg cga cac ctg gcc aag ctc aaa agc acc tac gtg gac ggc ctc gag        1920
Trp Arg His Leu Ala Lys Leu Lys Ser Thr Tyr Val Asp Gly Leu Glu
625                 630                 635                 640 ccg ctc atc cat ccg gag acc ggc cgc atc cac acc acg ttc aac cag        1968
Pro Leu Ile His Pro Glu Thr Gly Arg Ile His Thr Thr Phe Asn Gln
                645                 650                 655 acg gtg acg gct acc ggg cgg ctt tcc tcg agc aac ccg aac ctg cag        2016
Thr Val Thr Ala Thr Gly Arg Leu Ser Ser Ser Asn Pro Asn Leu Gln
            660                 665                 670 aac atc ccg gtt cgc acc gag atg ggg cgg gag atc cgc agg gcg ttt        2064
Asn Ile Pro Val Arg Thr Glu Met Gly Arg Glu Ile Arg Arg Ala Phe
        675                 680                 685 gtg ccg cgg ccg ggc tgg aag ctc ctc tcg gcc gac tac gtc cag atc        2112
Val Pro Arg Pro Gly Trp Lys Leu Leu Ser Ala Asp Tyr Val Gln Ile
    690                 695                 700 gaa ctt cgc att ctg gcc gcg ctg agc ggc gac gag gcg ctt cgc cgg        2160
Glu Leu Arg Ile Leu Ala Ala Leu Ser Gly Asp Glu Ala Leu Arg Arg
705                 710                 715                 720 gcc ttt ctg gag gga cag gac atc cat acg gcc acg gca gcc cgc gtc        2208
Ala Phe Leu Glu Gly Gln Asp Ile His Thr Ala Thr Ala Ala Arg Val
                725                 730                 735 ttc aag gtg ccg ccc gag cag gtg acg ccc gag cag cgc cgc cgc gcc        2256
Phe Lys Val Pro Pro Glu Gln Val Thr Pro Glu Gln Arg Arg Arg Ala
            740                 745                 750 aag atg gtc aac tac ggc att ccc tac ggg att tcg gcc tgg ggg ctg        2304
Lys Met Val Asn Tyr Gly Ile Pro Tyr Gly Ile Ser Ala Trp Gly Leu
        755                 760                 765 gcg cag cgg ctt cgc tgc tcc acg cgc gag gcg cag gag ctt atc gaa        2352
Ala Gln Arg Leu Arg Cys Ser Thr Arg Glu Ala Gln Glu Leu Ile Glu
    770                 775                 780 gaa tat cag cgg gcc ttt ccg ggc gtg acg cgc tac ctg cac cgc gtc        2400
Glu Tyr Gln Arg Ala Phe Pro Gly Val Thr Arg Tyr Leu His Arg Val
785                 790                 795                 800 gtc gaa gag gcc cgc cag aag ggc tac gtc gag acg ctg ctg ggc cgc        2448
```

```
Val Glu Glu Ala Arg Gln Lys Gly Tyr Val Glu Thr Leu Leu Gly Arg
            805                 810                 815 cgc cgc tac gta ccg aac atc aac tcc cgc aac cgg gcc gag cgc tcg    2496
Arg Arg Tyr Val Pro Asn Ile Asn Ser Arg Asn Arg Ala Glu Arg Ser
        820                 825                 830 atg gcc gaa cgc atc gcc gtg aac atg ccc atc cag ggc acg cag gcc    2544
Met Ala Glu Arg Ile Ala Val Asn Met Pro Ile Gln Gly Thr Gln Ala
    835                 840                 845 gac atg atc aag ctg gcc atg gtg cac atc tac cac cga ctg aag cgg    2592
Asp Met Ile Lys Leu Ala Met Val His Ile Tyr His Arg Leu Lys Arg
850                 855                 860 gaa ggc tac cgg gcc aag atg ctg ctc cag gtg cac gac gag ctg gtc    2640
Glu Gly Tyr Arg Ala Lys Met Leu Leu Gln Val His Asp Glu Leu Val
865                 870                 875                 880 ttc gag atg ccc ccc gaa gag gtg gag ccc gtg cgc caa ctg gtc gag    2688
Phe Glu Met Pro Pro Glu Glu Val Glu Pro Val Arg Gln Leu Val Glu
                885                 890                 895 cag gag atg aag cag gcc ctg ccg ctg gaa ggt gtg ccc atc gag gtg    2736
Gln Glu Met Lys Gln Ala Leu Pro Leu Glu Gly Val Pro Ile Glu Val
            900                 905                 910 gac atc ggc gtc ggc gac aac tgg ctg gat gcc cac tga                2775
Asp Ile Gly Val Gly Asp Asn Trp Leu Asp Ala His
            915                 920

<210> SEQ ID NO 2
<211> LENGTH: 924
<212> TYPE: PRT
<213> ORGANISM: Rhodothermus obamensis

<400> SEQUENCE: 2

Met Gln Arg Leu Tyr Leu Ile Asp Ala Met Ala Leu Ala Tyr Arg Ala
 1               5                  10                  15

Gln Tyr Val Phe Ile Ser Arg Pro Leu Val Asn Ser Lys Gly Gln Asn
            20                  25                  30

Thr Ser Ala Ala Tyr Gly Phe Thr Thr Ser Leu Leu Lys Leu Ile Glu
        35                  40                  45

Glu His Gly Met Asp Tyr Met Ala Val Val Phe Asp Ala Gly Gly Glu
    50                  55                  60

Glu Gly Thr Phe Arg Glu Ala Ile Tyr Glu Glu Tyr Lys Ala His Arg
65                  70                  75                  80

Glu Pro Pro Pro Glu Asp Leu Leu Ala Asn Leu Pro Trp Ile Lys Glu
                85                  90                  95

Ile Val Arg Ala Leu Asp Ile Pro Val Ile Glu Glu Pro Gly Val Glu
            100                 105                 110

Ala Asp Asp Val Ile Gly Thr Leu Ala Arg Arg Ala Glu Ala His Gly
        115                 120                 125

Ile Asp Val Val Ile Val Ser Pro Asp Lys Asp Phe Leu Gln Leu Leu
    130                 135                 140

Ser Pro His Val Ser Ile Tyr Lys Pro Ala Arg Arg Gly Glu Thr Phe
145                 150                 155                 160

Asp Leu Ile Thr Ile Glu Thr Phe Arg Glu Thr Tyr Gly Leu Glu Pro
                165                 170                 175

His Gln Phe Ile Asp Val Leu Ala Leu Met Gly Asp Pro Ser Asp Asn
            180                 185                 190

Val Pro Gly Val Pro Gly Ile Gly Glu Lys Thr Ala Val Gln Leu Ile
        195                 200                 205

Gln Gln Tyr Gly Ser Val Glu Asn Leu Leu Ala His Ala Glu Glu Val
```

```
            210                 215                 220
Lys Gly Lys Arg Ala Arg Glu Gly Leu Leu Asn His Arg Glu Glu Ala
225                 230                 235                 240
Leu Leu Ser Lys Arg Leu Val Thr Ile Arg Thr Asp Val Pro Leu Arg
                245                 250                 255
Ile Arg Trp Glu Ala Phe His Arg Ala Arg Pro Asp Leu Pro Arg Leu
                260                 265                 270
Leu Gln Ile Phe Gln Glu Leu Glu Phe Asp Ser Leu Val Arg Arg Ile
                275                 280                 285
Arg Glu Gly Gly Leu Ala Gly Ile Val Asn Gly Glu Ala Ala Leu Asp
                290                 295                 300
Glu Ala Leu Glu Ala Glu Thr Glu Pro Glu Phe Asp Phe Gly Pro Tyr
305                 310                 315                 320
Glu Pro Leu Gln Val Tyr Asp Pro Glu Lys Ala Asp Tyr Arg Ile Val
                325                 330                 335
Arg Asn Arg Gln Gln Leu Asp Glu Leu Val Ala His Leu Asp Gly Phe
                340                 345                 350
Glu Arg Leu Ala Ile Asp Thr Glu Thr Thr Ser Thr Glu Ala Met Trp
                355                 360                 365
Ala Ser Leu Val Gly Ile Ala Phe Ser Trp Glu Lys Gly Gln Gly Tyr
370                 375                 380
Tyr Val Pro Thr Pro Leu Pro Asp Gly Thr Pro Thr Glu Thr Val Leu
385                 390                 395                 400
Glu Arg Leu Ala Pro Ile Leu Arg Arg Ala Gln Arg Lys Val Gly Gln
                405                 410                 415
Asn Leu Lys Tyr Asp Leu Val Val Leu Ala Arg His Gly Val Gln Val
                420                 425                 430
Pro Pro Pro Tyr Phe Asp Thr Met Val Ala His Tyr Leu Ile Ala Pro
                435                 440                 445
Glu Glu Pro His Asn Leu Asp Val Leu Ala Arg Gln Tyr Leu Arg Tyr
                450                 455                 460
Gln Met Val Ser Ile Thr Glu Leu Ile Gly Ser Gly Arg Asp Gln Lys
465                 470                 475                 480
Ser Met Arg Asp Val Ser Ile Asp Glu Val Gly Pro Tyr Ala Cys Glu
                485                 490                 495
Asp Thr Asp Ile Ala Leu Gln Leu Ala Asp Val Leu Ala Ala Glu Leu
                500                 505                 510
Asp Arg His Gly Leu Arg His Ile Ala Glu Glu Met Glu Phe Pro Leu
                515                 520                 525
Ile Glu Val Leu Ala Asp Met Glu Arg Thr Gly Ile Cys Ile Asp Arg
                530                 535                 540
Ala Val Leu Arg Glu Ile Gly Lys Gln Leu Glu Ala Glu Leu His Glu
545                 550                 555                 560
Leu Glu Val Lys Ile Tyr Glu Val Ala Gly Val Glu Phe Asn Ile Gly
                565                 570                 575
Ser Pro Gln Gln Leu Ala Asp Val Leu Phe Lys Lys Leu Gly Leu Lys
                580                 585                 590
Pro Arg Ala Arg Thr Ser Thr Gly Arg Pro Ser Thr Lys Glu Ser Val
                595                 600                 605
Leu Gln Glu Leu Ala Thr Gln His Pro Leu Pro Gly Leu Ile Leu Asp
                610                 615                 620
Trp Arg His Leu Ala Lys Leu Lys Ser Thr Tyr Val Asp Gly Leu Glu
625                 630                 635                 640
```

```
Pro Leu Ile His Pro Glu Thr Gly Arg Ile His Thr Thr Phe Asn Gln
            645                 650                 655

Thr Val Thr Ala Thr Gly Arg Leu Ser Ser Ser Asn Pro Asn Leu Gln
            660                 665                 670

Asn Ile Pro Val Arg Thr Glu Met Gly Arg Glu Ile Arg Arg Ala Phe
            675                 680                 685

Val Pro Arg Pro Gly Trp Lys Leu Leu Ser Ala Asp Tyr Val Gln Ile
            690                 695                 700

Glu Leu Arg Ile Leu Ala Ala Leu Ser Gly Asp Glu Ala Leu Arg Arg
705                 710                 715                 720

Ala Phe Leu Glu Gly Gln Asp Ile His Thr Ala Thr Ala Ala Arg Val
            725                 730                 735

Phe Lys Val Pro Pro Glu Gln Val Thr Pro Glu Gln Arg Arg Arg Ala
            740                 745                 750

Lys Met Val Asn Tyr Gly Ile Pro Tyr Gly Ile Ser Ala Trp Gly Leu
            755                 760                 765

Ala Gln Arg Leu Arg Cys Ser Thr Arg Glu Ala Gln Glu Leu Ile Glu
            770                 775                 780

Glu Tyr Gln Arg Ala Phe Pro Gly Val Thr Arg Tyr Leu His Arg Val
785                 790                 795                 800

Val Glu Ala Arg Gln Lys Gly Tyr Val Glu Thr Leu Leu Gly Arg
            805                 810                 815

Arg Arg Tyr Val Pro Asn Ile Asn Ser Arg Asn Arg Ala Glu Arg Ser
            820                 825                 830

Met Ala Glu Arg Ile Ala Val Asn Met Pro Ile Gln Gly Thr Gln Ala
            835                 840                 845

Asp Met Ile Lys Leu Ala Met Val His Ile Tyr His Arg Leu Lys Arg
850                 855                 860

Glu Gly Tyr Arg Ala Lys Met Leu Leu Gln Val His Asp Glu Leu Val
865                 870                 875                 880

Phe Glu Met Pro Pro Glu Glu Val Glu Pro Val Arg Gln Leu Val Glu
            885                 890                 895

Gln Glu Met Lys Gln Ala Leu Pro Leu Glu Gly Val Pro Ile Glu Val
            900                 905                 910

Asp Ile Gly Val Gly Asp Asn Trp Leu Asp Ala His
            915                 920

<210> SEQ ID NO 3
<211> LENGTH: 1887
<212> TYPE: DNA
<213> ORGANISM: Rhodothermus obamensis
<220> FEATURE:
<221> NAME/KEY: CDS
<222> LOCATION: (1)..(1884)

<400> SEQUENCE: 3 atg aac ggc gaa gcc gcc ttg gat gag gcg ctt gaa gcg gag acc gag      48
Met Asn Gly Glu Ala Ala Leu Asp Glu Ala Leu Glu Ala Glu Thr Glu
 1               5                  10                  15 ccg gag ttc gat ttc ggg cca tac gag ccg ctg cag gtg tac gat ccg      96
Pro Glu Phe Asp Phe Gly Pro Tyr Glu Pro Leu Gln Val Tyr Asp Pro
            20                  25                  30 gaa aag gcg gac tac cgg atc gtc cgc aac cgc cag cag ctc gac gaa     144
Glu Lys Ala Asp Tyr Arg Ile Val Arg Asn Arg Gln Gln Leu Asp Glu
        35                  40                  45 ctc gtg gcg cat ctg gac gga ttc gaa cgg ctg gcc atc gac acg gag     192
```

```
                Leu Val Ala His Leu Asp Gly Phe Glu Arg Leu Ala Ile Asp Thr Glu
                             50                  55                  60 acg act tcg acc gag gcc atg tgg gcc tcg ctg gtg ggc att gcc ttt           240
Thr Thr Ser Thr Glu Ala Met Trp Ala Ser Leu Val Gly Ile Ala Phe
 65                  70                  75                  80 tcc tgg gag aaa ggc cag ggc tac tac gtg ccc acg ccg ctg ccg gac           288
Ser Trp Glu Lys Gly Gln Gly Tyr Tyr Val Pro Thr Pro Leu Pro Asp
                 85                  90                  95 ggc acg ccg acc gag acg gtg ctc gag cga ctg gcg ccg atc ctc cga           336
Gly Thr Pro Thr Glu Thr Val Leu Glu Arg Leu Ala Pro Ile Leu Arg
                100                 105                 110 cgg gcg cag cgc aaa gtc ggt cag aac ctg aag tac gat ctg gtg gtg           384
Arg Ala Gln Arg Lys Val Gly Gln Asn Leu Lys Tyr Asp Leu Val Val
            115                 120                 125 ctg gcg cgg cac ggc gtc caa gtc ccg ccc ccg tac ttc gac acg atg           432
Leu Ala Arg His Gly Val Gln Val Pro Pro Pro Tyr Phe Asp Thr Met
        130                 135                 140 gtg gcg cac tac ctg att gcg ccc gag gaa ccg cat aac ctg gac gtg           480
Val Ala His Tyr Leu Ile Ala Pro Glu Glu Pro His Asn Leu Asp Val
145                 150                 155                 160 ctg gcc cgc cag tac ctt cgc tac cag atg gtt tcc atc acg gaa ctg           528
Leu Ala Arg Gln Tyr Leu Arg Tyr Gln Met Val Ser Ile Thr Glu Leu
                165                 170                 175 atc ggc tcg ggt cgc gac cag aag tcc atg cgc gac gtg tcg atc gac           576
Ile Gly Ser Gly Arg Asp Gln Lys Ser Met Arg Asp Val Ser Ile Asp
            180                 185                 190 gag gtg ggg ccc tat gcc tgt gaa gac acg gac att gcg ctg caa ctg           624
Glu Val Gly Pro Tyr Ala Cys Glu Asp Thr Asp Ile Ala Leu Gln Leu
        195                 200                 205 gcc gat gtg ctg gcc gcc gag ttg gac cga cac gga ctc cgg cat atc           672
Ala Asp Val Leu Ala Ala Glu Leu Asp Arg His Gly Leu Arg His Ile
210                 215                 220 gcc gag gag atg gag ttc ccg ctc atc gag gtg ctg gcc gat atg gag           720
Ala Glu Glu Met Glu Phe Pro Leu Ile Glu Val Leu Ala Asp Met Glu
                225                 230                 235                 240 cgg acg ggc atc tgc atc gat cgc gcg gtg ctt cgg gaa atc ggt aag           768
Arg Thr Gly Ile Cys Ile Asp Arg Ala Val Leu Arg Glu Ile Gly Lys
            245                 250                 255 caa ctc gaa gcg gag ctt cac gaa ctg gag gtg aag atc tat gag gtg           816
Gln Leu Glu Ala Glu Leu His Glu Leu Glu Val Lys Ile Tyr Glu Val
        260                 265                 270 gcc ggc gtc gaa ttc aac atc ggc tcg ccg cag caa ctg gcg gac gtc           864
Ala Gly Val Glu Phe Asn Ile Gly Ser Pro Gln Gln Leu Ala Asp Val
            275                 280                 285 ttg ttc aag aag ctc ggg ttg aag ccg cgg gcg cgc acc agc acc ggc           912
Leu Phe Lys Lys Leu Gly Leu Lys Pro Arg Ala Arg Thr Ser Thr Gly
290                 295                 300 cgg cct tcc acc aaa gag agc gtg ctg cag gag ctg gcc acg cag cac           960
Arg Pro Ser Thr Lys Glu Ser Val Leu Gln Glu Leu Ala Thr Gln His
305                 310                 315                 320 ccg ctc ccc ggc ctg atc ctg gac tgg cga cac ctg gcc aag ctc aaa          1008
Pro Leu Pro Gly Leu Ile Leu Asp Trp Arg His Leu Ala Lys Leu Lys
                325                 330                 335 agc acc tac gtg gac ggc ctc gag ccg ctc atc cat ccg gag acc ggc          1056
Ser Thr Tyr Val Asp Gly Leu Glu Pro Leu Ile His Pro Glu Thr Gly
            340                 345                 350 cgc atc cac acc acg ttc aac cag acg gtg acg gct acc ggg cgg ctt          1104
Arg Ile His Thr Thr Phe Asn Gln Thr Val Thr Ala Thr Gly Arg Leu
        355                 360                 365
```

```
tcc tcg agc aac ccg aac ctg cag aac atc ccg gtt cgc acc gag atg    1152
Ser Ser Ser Asn Pro Asn Leu Gln Asn Ile Pro Val Arg Thr Glu Met
    370                 375                 380 ggg cgg gag atc cgc agg gcg ttt gtg ccg cgg ccg ggc tgg aag ctg    1200
Gly Arg Glu Ile Arg Arg Ala Phe Val Pro Arg Pro Gly Trp Lys Leu
385                 390                 395                 400 ctc tcg gcc gac tac gtc cag atc gaa ctt cgc att ctg gcc gcg ctg    1248
Leu Ser Ala Asp Tyr Val Gln Ile Glu Leu Arg Ile Leu Ala Ala Leu
                405                 410                 415 agc ggc gac gag gcg ctt cgc cgg gcc ttt ctg gag gga cag gac atc    1296
Ser Gly Asp Glu Ala Leu Arg Arg Ala Phe Leu Glu Gly Gln Asp Ile
            420                 425                 430 cat acg gcc acg gca gcc cgc gtc ttc aag gtg ccg ccc gag cag gtg    1344
His Thr Ala Thr Ala Ala Arg Val Phe Lys Val Pro Pro Glu Gln Val
        435                 440                 445 acg ccc gag cag cgc cgc cgc gcc aag atg gtc aac tac ggc att ccc    1392
Thr Pro Glu Gln Arg Arg Arg Ala Lys Met Val Asn Tyr Gly Ile Pro
    450                 455                 460 tac ggg att tcg gcc tgg ggg ctg gcg cag cgg ctt cgc tgc tcc acg    1440
Tyr Gly Ile Ser Ala Trp Gly Leu Ala Gln Arg Leu Arg Cys Ser Thr
465                 470                 475                 480 cgc gag gcg cag gag ctt atc gaa gaa tat cag cgg gcc ttt ccg ggc    1488
Arg Glu Ala Gln Glu Leu Ile Glu Glu Tyr Gln Arg Ala Phe Pro Gly
                485                 490                 495 gtg acg cgc tac ctg cac cgc gtc gtc gaa gag gcc cgc cag aag ggc    1536
Val Thr Arg Tyr Leu His Arg Val Val Glu Glu Ala Arg Gln Lys Gly
            500                 505                 510 tac gtc gag acg ctg ctg ggc cgc cgc cgc tac gta ccg aac atc aac    1584
Tyr Val Glu Thr Leu Leu Gly Arg Arg Arg Tyr Val Pro Asn Ile Asn
        515                 520                 525 tcc cgc aac cgg gcc gag cgc tcg atg gcc gaa cgc atc gcc gtg aac    1632
Ser Arg Asn Arg Ala Glu Arg Ser Met Ala Glu Arg Ile Ala Val Asn
    530                 535                 540 atg ccc atc cag ggc acg cag gcc gac atg atc aag ctg gcc atg gtg    1680
Met Pro Ile Gln Gly Thr Gln Ala Asp Met Ile Lys Leu Ala Met Val
545                 550                 555                 560 cac atc tac cac cga ctg aag cgg gaa ggc tac cgg gcc aag atg ctg    1728
His Ile Tyr His Arg Leu Lys Arg Glu Gly Tyr Arg Ala Lys Met Leu
                565                 570                 575 ctc cag gtg cac gac gag ctg gtc ttc gag atg ccc ccc gaa gag gtg    1776
Leu Gln Val His Asp Glu Leu Val Phe Glu Met Pro Pro Glu Glu Val
            580                 585                 590 gag ccc gtg cgc caa ctg gtc gag cag gag atg aag cag gcc ctg ccg    1824
Glu Pro Val Arg Gln Leu Val Glu Gln Glu Met Lys Gln Ala Leu Pro
        595                 600                 605 ctg gaa ggt gtg ccc atc gag gtg gac atc ggc gtc ggc gac aac tgg    1872
Leu Glu Gly Val Pro Ile Glu Val Asp Ile Gly Val Gly Asp Asn Trp
    610                 615                 620 ctg gat gcc cac tga                                                 1887
Leu Asp Ala His
625

<210> SEQ ID NO 4
<211> LENGTH: 628
<212> TYPE: PRT
<213> ORGANISM: Rhodothermus obamensis

<400> SEQUENCE: 4

Met Asn Gly Glu Ala Ala Leu Asp Glu Ala Leu Glu Ala Glu Thr Glu
 1               5                  10                  15
```

-continued

```
Pro Glu Phe Asp Phe Gly Pro Tyr Glu Pro Leu Gln Val Tyr Asp Pro
         20                  25                  30

Glu Lys Ala Asp Tyr Arg Ile Val Arg Asn Arg Gln Gln Leu Asp Glu
         35                  40                  45

Leu Val Ala His Leu Asp Gly Phe Glu Arg Leu Ala Ile Asp Thr Glu
         50                  55                  60

Thr Thr Ser Thr Glu Ala Met Trp Ala Ser Leu Val Gly Ile Ala Phe
 65                  70                  75                  80

Ser Trp Glu Lys Gly Gln Gly Tyr Tyr Val Pro Thr Pro Leu Pro Asp
             85                  90                  95

Gly Thr Pro Thr Glu Thr Val Leu Glu Arg Leu Ala Pro Ile Leu Arg
            100                 105                 110

Arg Ala Gln Arg Lys Val Gly Gln Asn Leu Lys Tyr Asp Leu Val Val
            115                 120                 125

Leu Ala Arg His Gly Val Gln Val Pro Pro Tyr Phe Asp Thr Met
        130                 135                 140

Val Ala His Tyr Leu Ile Ala Pro Glu Pro His Asn Leu Asp Val
145                 150                 155                 160

Leu Ala Arg Gln Tyr Leu Arg Tyr Gln Met Val Ser Ile Thr Glu Leu
                165                 170                 175

Ile Gly Ser Gly Arg Asp Gln Lys Ser Met Arg Asp Val Ser Ile Asp
            180                 185                 190

Glu Val Gly Pro Tyr Ala Cys Glu Asp Thr Asp Ile Ala Leu Gln Leu
            195                 200                 205

Ala Asp Val Leu Ala Ala Glu Leu Asp Arg His Gly Leu Arg His Ile
        210                 215                 220

Ala Glu Glu Met Glu Phe Pro Leu Ile Glu Val Leu Ala Asp Met Glu
225                 230                 235                 240

Arg Thr Gly Ile Cys Ile Asp Arg Ala Val Leu Arg Glu Ile Gly Lys
                245                 250                 255

Gln Leu Glu Ala Glu Leu His Glu Leu Glu Val Lys Ile Tyr Glu Val
            260                 265                 270

Ala Gly Val Glu Phe Asn Ile Gly Ser Pro Gln Gln Leu Ala Asp Val
            275                 280                 285

Leu Phe Lys Lys Leu Gly Leu Lys Pro Arg Ala Arg Thr Ser Thr Gly
        290                 295                 300

Arg Pro Ser Thr Lys Glu Ser Val Leu Gln Glu Leu Ala Thr Gln His
305                 310                 315                 320

Pro Leu Pro Gly Leu Ile Leu Asp Trp Arg His Leu Ala Lys Leu Lys
                325                 330                 335

Ser Thr Tyr Val Asp Gly Leu Glu Pro Leu Ile His Pro Glu Thr Gly
            340                 345                 350

Arg Ile His Thr Thr Phe Asn Gln Thr Val Thr Ala Thr Gly Arg Leu
            355                 360                 365

Ser Ser Ser Asn Pro Asn Leu Gln Asn Ile Pro Val Arg Thr Glu Met
        370                 375                 380

Gly Arg Glu Ile Arg Arg Ala Phe Val Pro Arg Pro Gly Trp Lys Leu
385                 390                 395                 400

Leu Ser Ala Asp Tyr Val Gln Ile Glu Leu Arg Ile Leu Ala Ala Leu
                405                 410                 415

Ser Gly Asp Glu Ala Leu Arg Arg Ala Phe Leu Glu Gly Gln Asp Ile
            420                 425                 430

His Thr Ala Thr Ala Ala Arg Val Phe Lys Val Pro Pro Glu Gln Val
```

```
                435                 440                 445
Thr Pro Glu Gln Arg Arg Ala Lys Met Val Asn Tyr Gly Ile Pro
    450                 455                 460
Tyr Gly Ile Ser Ala Trp Gly Leu Ala Gln Arg Leu Arg Cys Ser Thr
465                 470                 475                 480
Arg Glu Ala Gln Glu Leu Ile Glu Glu Tyr Gln Arg Ala Phe Pro Gly
                485                 490                 495
Val Thr Arg Tyr Leu His Arg Val Val Glu Glu Ala Arg Gln Lys Gly
                500                 505                 510
Tyr Val Glu Thr Leu Leu Gly Arg Arg Tyr Val Pro Asn Ile Asn
                515                 520                 525
Ser Arg Asn Arg Ala Glu Arg Ser Met Ala Glu Arg Ile Ala Val Asn
530                 535                 540
Met Pro Ile Gln Gly Thr Gln Ala Asp Met Ile Lys Leu Ala Met Val
545                 550                 555                 560
His Ile Tyr His Arg Leu Lys Arg Glu Gly Tyr Arg Ala Lys Met Leu
                565                 570                 575
Leu Gln Val His Asp Glu Leu Val Phe Glu Met Pro Pro Glu Glu Val
                580                 585                 590
Glu Pro Val Arg Gln Leu Val Glu Gln Glu Met Lys Gln Ala Leu Pro
                595                 600                 605
Leu Glu Gly Val Pro Ile Glu Val Asp Ile Gly Val Gly Asp Asn Trp
        610                 615                 620
Leu Asp Ala His
625

<210> SEQ ID NO 5
<211> LENGTH: 26
<212> TYPE: DNA
<213> ORGANISM: synthetic

<400> SEQUENCE: 5
tccgayccca acctscagaa catccc                                      26

<210> SEQ ID NO 6
<211> LENGTH: 23
<212> TYPE: DNA
<213> ORGANISM: Synthetic

<400> SEQUENCE: 6
aggassagct cgtcgtgsac ctg                                         23

<210> SEQ ID NO 7
<211> LENGTH: 21
<212> TYPE: DNA
<213> ORGANISM: synthetic

<400> SEQUENCE: 7
cgcagggcgt ttgtgccgcg g                                           21

<210> SEQ ID NO 8
<211> LENGTH: 21
<212> TYPE: DNA
<213> ORGANISM: synthetic

<400> SEQUENCE: 8
gtctcccgcc ccatctcggt g                                           21
```

<210> SEQ ID NO 9
<211> LENGTH: 21
<212> TYPE: DNA
<213> ORGANISM: synthetic

<400> SEQUENCE: 9
gccggccgct tgtcaactcg a                                                    21

<210> SEQ ID NO 10
<211> LENGTH: 21
<212> TYPE: DNA
<213> ORGANISM: synthetic

<400> SEQUENCE: 10
tgatgaacac gtattgcgcc c                                                    21

<210> SEQ ID NO 11
<211> LENGTH: 24
<212> TYPE: DNA
<213> ORGANISM: Synthetic

<400> SEQUENCE: 11
gaagcgggaa ggctaccggg ccaa                                                 24

<210> SEQ ID NO 12
<211> LENGTH: 24
<212> TYPE: DNA
<213> ORGANISM: Synthetic

<400> SEQUENCE: 12
agtcggtggt agatgtgcac catg                                                 24

<210> SEQ ID NO 13
<211> LENGTH: 39
<212> TYPE: DNA
<213> ORGANISM: Synthetic

<400> SEQUENCE: 13
ctggccggcc atatgaacgg cgaagccgcc ttggatgag                                 39

<210> SEQ ID NO 14
<211> LENGTH: 36
<212> TYPE: DNA
<213> ORGANISM: Synthetic

<400> SEQUENCE: 14
gttggatccg cttcagtggg catccagcca gttgtc                                    36

<210> SEQ ID NO 15
<211> LENGTH: 15
<212> TYPE: PRT
<213> ORGANISM: Escherichia coli

<400> SEQUENCE: 15

Ala Ala Lys Asp Val Lys Phe Gly Asn Asp Ala Arg Val Lys Met
 1               5                  10                  15